United States Patent
Tanner et al.

(10) Patent No.: US 11,827,885 B1
(45) Date of Patent: Nov. 28, 2023

(54) RNASE INHIBITORS

(71) Applicant: New England Biolabs, Inc., Ipswich, MA (US)

(72) Inventors: Nathan Tanner, West Newbury, MA (US); Jennifer Ong, Salem, MA (US); Esta Slayton, Epping, NH (US); Lisa Maduzia, Topsfield, MA (US); Salvatore V. Russello, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 137 days.

(21) Appl. No.: 17/207,507

(22) Filed: Mar. 19, 2021

Related U.S. Application Data

(60) Provisional application No. 63/001,417, filed on Mar. 29, 2020, provisional application No. 62/992,921, filed on Mar. 21, 2020.

(51) Int. Cl.
| | | |
|---|---|---|
| *C12N 15/11* | (2006.01) | |
| *C12N 15/113* | (2010.01) | |
| *C12N 15/10* | (2006.01) | |
| *C12N 9/12* | (2006.01) | |
| *C12Q 1/6848* | (2018.01) | |
| *C12N 9/58* | (2006.01) | |

(52) U.S. Cl.
CPC ........ *C12N 15/1137* (2013.01); *C12N 9/1247* (2013.01); *C12N 9/1276* (2013.01); *C12N 15/1003* (2013.01); *C12Q 1/6848* (2013.01); *C12N 9/58* (2013.01); *C12N 2310/16* (2013.01); *C12Y 207/07006* (2013.01); *C12Y 207/07049* (2013.01)

(58) Field of Classification Search
CPC .................................................. C12N 2310/16
See application file for complete search history.

(56) References Cited

U.S. PATENT DOCUMENTS

| | | |
|---|---|---|
| 3,975,388 A | 8/1976 | Hakim et al. |
| 10,633,644 B1 | 4/2020 | Chen et al. |
| 2010/0240550 A1 * | 9/2010 | Jackson ............... C12Q 1/6837 506/13 |

FOREIGN PATENT DOCUMENTS

WO   WO-2005083081 A1 *   9/2005   ............. C07K 16/40

OTHER PUBLICATIONS

Tuerk, et al. (1990), Science 249 p. 505-10.
Blackwell, et al. (1990) Science 250 1104-10.
Gold, et al . . . 2010. PLoS One vol. 5.
Stoltenburg, et al. (2015) Plos One vol. 10.
Wu, et al. (2016), Methods 106, 21-28.

\* cited by examiner

*Primary Examiner* — Ekaterina Poliakova-Georgantas
*Assistant Examiner* — Ekaterina Poliakova
(74) *Attorney, Agent, or Firm* — New England Biolabs, Inc

(57) ABSTRACT

Compositions, methods and kits are provided that include an inhibitory oligonucleotide RNase inhibitor capable of inhibiting one or more types of RNase that coexist with biological samples or are introduced in the laboratory, thereby protecting RNA in the sample from degradation. More than one type of oligonucleotide RNase inhibitor may be combined in a mixture to inhibit a plurality of different RNases. Single oligonucleotides were identified to have inhibitory activity for a plurality of different RNases. The RNase oligonucleotide inhibitor may be immobilized on beads or other surface. It may be stored in a lyophilized form or in solution.

11 Claims, 12 Drawing Sheets

Specification includes a Sequence Listing.

| Name | Sequence (5-3) |
|---|---|
| SEQ ID NO. 1 | CAGTCTGAGGAACATATATAAACGGCTCTGGACTATATTGTGAGAATGGCTCCCTCAGACTG |
| SEQ ID NO. 2 | CAGTCTGAGGATTAGAGGACTAGAATTGGGCGTTTAGGCGTTGGGGACCCCTCAGACTG |
| SEQ ID NO. 3 | CAGTCTGAGGCCATGTCACCATTGTCAATTGGTTGTTATAAAACAAGGCGATACAATCATCCCTCAGACTG |
| SEQ ID NO. 4 | CAGTCTGAGGGGTTGTTGAATACCTCCTTATATAGACCTTGAGACCCTCGATTGCCGACGCAGGCTAACCTCAGACTG |
| SEQ ID NO. 5 | CAGTCTGAGGTATACCCTTATATAGACCTTGAGACCCTCGATTGCCGACGCAGGCTAACCTCAGACTG |
| SEQ ID NO. 6 | CAGTCTGAGGTCAAGATGCACTTGAGATGCCAGATGCCTCCATAGATAGCCTCCTCAGACTG |
| SEQ ID NO. 7 | CAGTCTGAGGCCTCAGCCGCTGGTAAGGTTTAGCGGTTGGCAGGGATGAGCCTCAGACTG |
| SEQ ID NO. 8 | CAGTCTGAGGATTGCCGACACGCCACAATTGGGGCCTTTGGGACAGGTGGGGCCCTCAGACTG |
| SEQ ID NO. 9 | CAGTCTGAGGAAGCTACTGATATCGTGAATGCAGTTCGATGTGGAGCAGTCTACAGACTG |
| SEQ ID NO. 10 | CAGTCTGAGGACACAAGAGGTTTCGAATGCATTTCGATGCAGTGTTTATGGGGTGCATCCTACACAGTCGCTGCGTAGCAAGTACA |
| SEQ ID NO. 11 | AGCAGTCCGAAGTGAGTGACTGACTGACATTAGACCTATGTCGTGAGTCTGCGTTGGGTACATTTAACTGGTAGAGCTGCGTAGCAAGTCGCTGCGTAGCAAGTACA |
| SEQ ID NO. 12 | AGCAGTCCGAAGTGAGTGACTGACTGACATTAGACCTCGCTTGGGTACATCGGCCGTGGTCTGCAGACACTCACTCAGCGATTAGCAAGTCGCTGCGTAGCAAGTACA |
| SEQ ID NO. 13 | AGCAGTCCGAAGTGAGTGACTGACTGACGGCCGTGGTCTGTTATCAGACACTCACTCATGGGTGGGGTTTTTCACCTATATCGGAGTGCGTAGCAAGTACA |
| SEQ ID NO. 14 | AGCAGTCCGAAGTGAGTGACTGACTGACATGCCATCATGGGTCTGTTTATCAGACACTCACTCAGCGATTTATGGGTCTATGCAATTATGAGTGAGTTAGTCGCTGCGTAGCAAGTACA |
| SEQ ID NO. 15 | AGCAGTCCGAAGTGAGTGACTGACTGACAATGCCCGCCCTTTAAACCCGGTACTTAGTCGCTGCGTAGCAAGTACA |
| SEQ ID NO. 16 | AGCAGTCCGAAGTGAGTGACTGACTGACATCGAGCCTAAGTAGGGTTTTTTAAACCCGCGAGTGCCCTCAGTGCCTCCAGTCGCTGCGTAGCAAGTACA |
| SEQ ID NO. 17 | AGCAGTCCGAAGTGAGTGACTGACTGACATGCTGTGCAGTGACATCGAGCCTCAGTAAGTTTTTAACCCCCATACCCTCAGTCAGTCCGGTCAGTCGCTGCGTAGCAAGTACA |
| SEQ ID NO. 18 | AGCAGTCCGAAGTGAGTGACTGACTGACAACTGGTGGATGTGTGATTCTAAATGTTGCACACCTAGAGTTATGCCGAACAAGGAAAGTCGCTGCGTAGCAAGTACA |
| SEQ ID NO. 19 | AGCAGTCCGAAGTGAGTGACTGACTGACTTAATCTCATTCATTAAGAATTTCGAACATTTCATATCAGCCGAAACATATAGGGTTCCAAAAGTCGCTGCGTAGCAAGTACA |
| SEQ ID NO. 20 | AGCAGTCCGAAGTGAGTGACTGACTGACATGAACTCATGAATCTCATATCTCATTACAGAATTAGCCCGTAATTATCACCTCCGGGAGCCTACGTCGCTGCGTAGCAAGTACA |
| SEQ ID NO. 21 | AGCAGTCCGAAGTGAGTGACTGACTGACAGGTGACATGAACTCATGAATCTCATATCTCATTACAGAATTAAAAATCGGGAACATGTAACTGTGAGGCGTAAGTCGCTGCGTAGCAAGTACA |
| SEQ ID NO. 22 | AGCAGTCCGAAGTGAGTGACTGACTGACATGAACTCATTAGTGCAATTAAAATCGGGAACATGTAACTGTGAGGCGTAACTGGGACTTGTGAAGCCTACTGGAAGTCGCTGCGTAGCAAGTACA |
| SEQ ID NO. 23 | AGCAGTCCGAAGTGAGTGACTGACTGACATCGGGAACATGTAACTGTGAGGCGTAACTGGGACCCTTGTCGCCCTCAGATGCAATATAAAAATCGGATTTAGGCATGTCGCTGCGTAGCAAGTACA |
| SEQ ID NO. 24 | AGCAGTCCGAAGTGAGTGACTGACTGACTTGTGAAGCCTACTGGACATGGTTTAGGCATGTCGCTGCGTAGCAAGTACA |
| SEQ ID NO. 25 | AGCAGTCCGAAGTGAGTGACTGACTGACCCCTTGTCGCCCTCAGATGCAATATCGGATTAGGCATGTCGCTGCGTAGCAAGTACA |
| SEQ ID NO. 26 | AGCAGTCCGAAGTGAGTGACTGACTGACCCTTGTCGCCCTCAGATGCAATATCCGTAGGTTCGTCGCTGCGTAGCAAGTACA |
| SEQ ID NO. 27 | AGCAGTCCGAAGTGAGTGACTGACTGACACCTAGGTTTCGCTCAGTAGTATGGAAAATAAGTCGCTGCGTAGCAAGTACA |
| SEQ ID NO. 28 | TTCGAATGCATTTCGAACATCGTATCAACATCTGTATCAAC |
| SEQ ID NO. 29 | TTCGAATGCATTTCGAACATCTGTATCAAC |
| SEQ ID NO. 30 | TTCGAATGCATTTCGAACATCTGTATCAACACCCTCAGACTG |

```
SEQ ID NO. 31  TTCGAATGCATTTCGAACATCTATATCAGC
SEQ ID NO. 32  AGCAAGAGAGCCTGCCTGTCCCCTGTCTTAGACCGCAAATGCACGTCTGCCTGTTTGGGACGTCCTACGCCCATCATCATCTACTAAAAAAAA
SEQ ID NO. 33  AGCAAGAGAGCCTGCCTGTCCTGTCTGCTACTCTGCCTCCCGTCTACTCTTAAGTCTCTAAGTCATTAATGCTCCGTAAACAGCAGACGACCTACGCCCATCATCATCTACTAAAAAAAA
SEQ ID NO. 34  AGCAAGAGAGCCTGCCTGTCCTGTCGCCTCGTCTGTCGCCCTCAGCGTGTCGCCCTCAGCGTGTCACTGCGTCGAGGGACTGCAGAGCCGGTAGCCACCTACGCCCATCATCATCTACTAAAAAAAA
SEQ ID NO. 35  AGCAAGAGAGCCTGCCTGTCCTGTCTGCCTGTCGCCTCTGTTGTAACACCCCTGATCCGTCCAATCTGGATTTAAAGCCTACCACTTAAAGCCTACGCCCATCATCATCTACTAAAAAAAA
SEQ ID NO. 36  AGCAAGAGAGCCTGCCTGTCCTGTCTGCCTCGTCGCCCTCAGCGTGTCACCCTGGATCCGTCCGATCCGGATCAATCTGGCCGACACGGCCAACCGACCTACGCCCATCATCATCTACTAAAAAAAA
SEQ ID NO. 37  AGCAAGAGAGCCTGCCTGTCCTGTCTGCCTGTCCCCTGTCTGTGCCCTCAGCGTGTCACTGCGTCCTGAACTAATTGCCACTGACGGGCCAACCGACCTACGCCCATCATCATCTACTAAAAAAAA
SEQ ID NO. 38  AGCAAGAGAGCCTGCCTGTCCTGTCCGCCTGTCCCCTGCCTGTCTGTAATGCCCCCGCGTAATCCCCCAGCGCGCGCCTACTTGGCTCCTGCTCGTTGGCTCCTACGCCCATCATCATCTACTAAAAAAAA
SEQ ID NO. 39  AGCAAGAGAGCCTGCCTGTCCTGTCTGCCTGTCTCTGTAATGCCCTCTACCCCGCGGCCATTCCCGCGGCCATCTGAGCGTTGTGCAGGATGTAGCAAACAGTTAACGCCTACGCCCATCATCATCTACTAAAAAAAA
SEQ ID NO. 40  AGCAAGAGAGCCTGCCTGTCCTGTCTGCCTGTCTCTGTAATCTGACCCCGCGGCCATTCCCAGCGTTGTCACTGCGGTCCGAGGGACTGCAGAGCCGGTAGCAACAGTTAACGCCTACGCCCATCATCATCTACTAAAAAAAA
SEQ ID NO. 41  AGCAAGAGAGCCTGCCTGTCCTGTCTGCCTGTCTGTCTGTCCTTTTAAGAACCCTCGACCTGACCGAAATGCACGTCTGCCTGTTTG
SEQ ID NO. 42  AGCAAGAGAGCCTGCCTGTCCTGTCTGCCTGTCCTGTCTTAGACCGCAAATGCACGTCTGCCTGTTTG
SEQ ID NO. 43  CCTGTCCCCTGTCTTAGACCGCAAATGCACGTCTGCCTGTTTG
SEQ ID NO. 44  TCCCCTGTCGCCTCCGTTCCAGTATACATTACCTGGTTAAACCTTGGC
SEQ ID NO. 45  TCTGTCGCCTCCGTTCCAGTATACATTACCTGGTTAAACCTTGGC
SEQ ID NO. 46  TCGCCTCCGTTCCAGTATACATTACCTGGTTAAACCTTGGCAACC
SEQ ID NO. 47  AGCAAGAGAGCCTGCCTGTCCTGTCACTGCGTCGAGGGA
SEQ ID NO. 48  AGAGCCTGCCTGTCTCGCCCTCAGCGTGTCACTGCGTCGAGGGACTGC
SEQ ID NO. 49  CCTGCCTGTCGCCCTCAGCGTGTCACTGCGTCGAGGGACTGCAGAG
SEQ ID NO. 50  CCTGTCGCCCTCAGCGTGTCACTGCGTCGAGGGACTGCAGAGCCGG
SEQ ID NO. 51  TCGCCTCAGCGTGTCACTGCGTCGAGGGACTGCAGAGCCGGTAGC
SEQ ID NO. 52  AGCAAGCCTGCCTGTCACTGCGTCGAGGGACTGCAGAGCCGGTAGCCACC
SEQ ID NO. 53  AGAGCCTGCCTGTCGCCCTCAGCGTGTCACTGCGTCGAGGGACTGCAGAG
SEQ ID NO. 54  CCTGCCGTGCCCTCAGCGCGCCCTAGCTGCCAGCCTACG
SEQ ID NO. 55  CCTGTCGCCGTGCCTCTTCAGCGCGCCCTAGCTGCCAGCCTACG
SEQ ID NO. 56  TTAAGAACACGGCGTGCCTCTTCAGCGCGCCTAGCTGCCAGCCTACG
SEQ ID NO. 57  GAACACGGGCGTGCCTCTTCAGCGCGCCTAGCTGCCAGCCTACG
SEQ ID NO. 58  ACGGCGTGCCTCTTCAGCGCGCCTAGCTGCCAGCCTACGCCCA
```

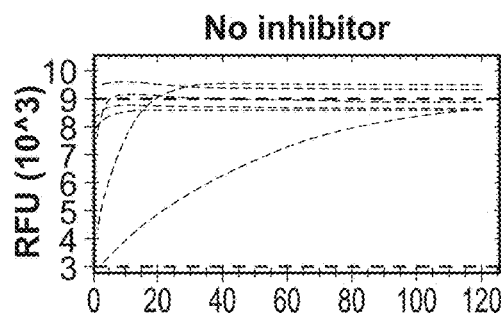
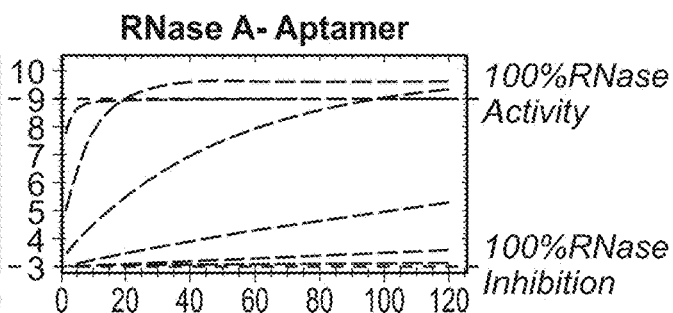
FIG. 3A  FIG. 3B
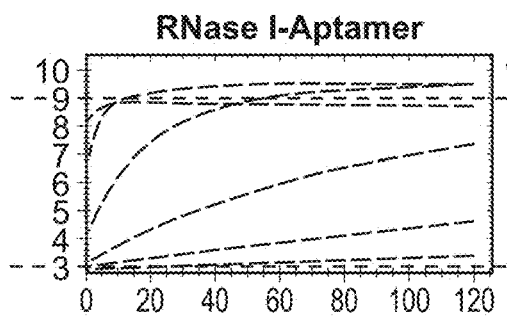
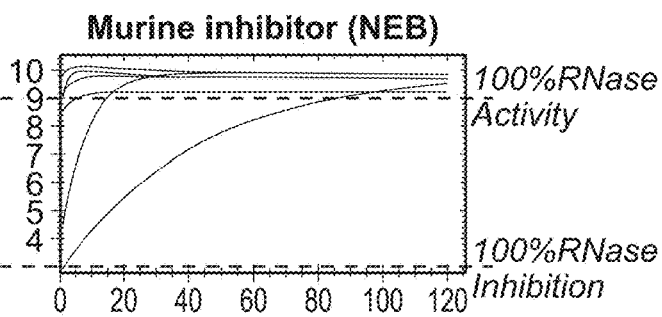
FIG. 3C  FIG. 3D
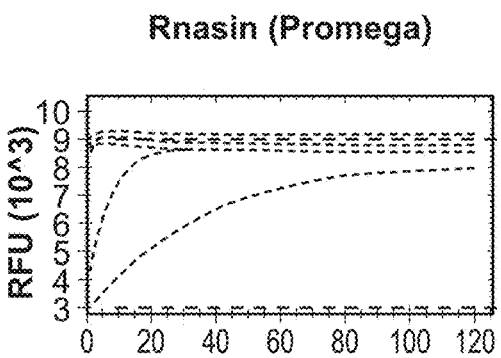
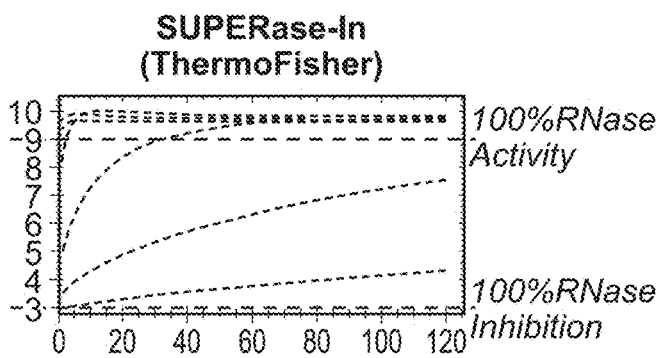
FIG. 3E  FIG. 3F
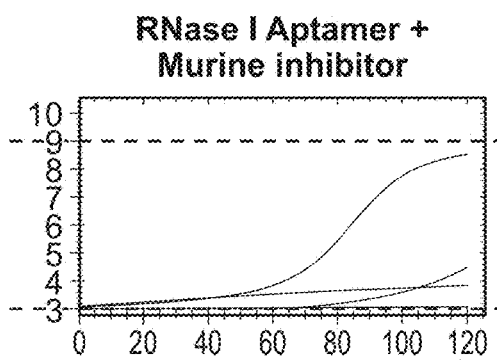
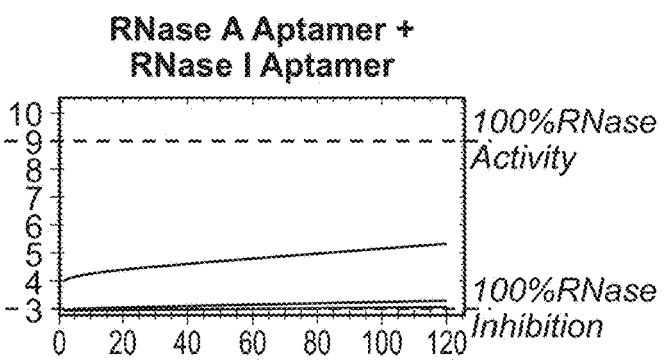
FIG. 3G  FIG. 3H

US 11,827,885 B1

RNASE INHIBITORS

CROSS REFERENCE

This application claims priority from U.S. Provisional Application Ser. No. 62/992,921, filed Mar. 21, 2020 and U.S. Provisional Application Ser. No. 63/001,417, filed Mar. 29, 2020, herein incorporated by reference.

BACKGROUND

RNases, or ribonucleases, are a broad class of RNA-degrading enzyme possessed by all organisms. In some contexts, RNases are desirable when the intention is to remove RNAs from a biological preparation but in those instances where RNAs are the subject of a study or purification protocol, it is important to remove the RNases. This is commonly achieved by the use of protein-based inhibitors or antibodies. These inhibitors are generally specific for a specific class of RNases. Most commonly, commercial inhibitors target RNase A that is found in eukaryotes. Less common are inhibitors against RNase I which is found in prokaryotes. RNase A is a very robust enzyme that is capable of withstanding temperatures as high as 100° C.

SUPERase-In™ (ThermoFisher Scientific, Waltham, MA) contains one or more antibodies that are described as inhibiting both RNase A and RNase I. This product is described as inactivating RNases at a temperature of 37° C.-65° C. and only release RNases in the presence of DTT. RNasin® Plus (Promega, Madison, WI) is a non-antibody protein that inhibits only RNase A but has a long term stability profile because it is stable up to 15 minutes at 70° C.

Because protein inhibitors bind non-covalently in a 1:1 ratio, a large amount of these inhibitors is required to inhibit RNase activity. This can be a costly solution as proteins are generally expensive to make and purify and to ensure that associated RNases derived from their manufacture are not carried into the samples. It would be desirable to obtain RNase inhibitors that are not only stable and effective against both prokaryotic and eukaryotic RNases but also that either bind more efficiently or are more cost effective for the identified purposes. Moreover, it would be desirable to avoid protein inhibitors that are synthesized in a biological context that itself has intrinsic RNases associated with their source. It would further be desirable to have a chemically synthesized non-protein inhibitor with a long shelf life, that is stable at high temperatures and is cost effective to manufacture in quantities suitable for inhibition of RNases in materials from natural sources.

SUMMARY

In general, a composition is provided that includes a single stranded oligonucleotide RNase inhibitor that inhibits the activity of at least one RNase having RNase A or RNase I activity. In one aspect, the inhibitor is stable at 90° C. for at least 15 minutes while retaining its ability to inhibit at least one of RNase A and RNase I activity associated with the RNase at 95° C. In one aspect, the inhibitor is capable of inhibiting RNase A and/or RNase I. In one aspect, the RNase inhibitor is an aptamer and has for example, a sequence length in the range of 20-100 nucleotides. In one embodiment, the RNase inhibitor has at least 90% sequence identity with a sequence selected from any of SEQ ID NOs: 1-62 for example at least 90% sequence identity with SEQ ID NO: 62. In an embodiment, the RNase inhibitor further includes hydrophobic nucleotide modifications.

The RNase inhibitor may be formulated for convenience by for example being in a solution, immobilized on a matrix or in powder form as a freeze dried or lyophilized preparation. The RNase inhibitor may be immobilized on a matrix selected from a bead, a reaction vessel or a multiwell plate wherein the reaction vessel or multi-well plate has a polymer surface.

The composition may further include a biological sample, a synthetic RNA and/or reagents for synthesizing RNA. The composition may further include a synthetic RNA. Examples of reagents included in the composition include an RNA polymerase that is not substantially reversibly inhibited or inhibited by the RNase inhibitor, a reverse transcriptase that is not substantially reversibly inhibited or inhibited by the RNase inhibitor, a proteinase such as Proteinase K that is optionally thermolabile.

In general, methods are provided for protecting an RNA in a sample from degradation by an RNase, comprising: combining any composition described above with a sample containing RNA or a reaction mixture for adding to or synthesizing RNA. For example, the RNase inhibitor used in the method is an oligonucleotide having a sequence with at least 90% identity to any of the sequences selected from SEQ ID NOs: 1-62. In embodiments, the method may include reverse transcribing the RNA with a reverse transcriptase to form DNA and amplifying the DNA for subsequent detection, diagnosis of the RNA, purification or sequencing. The method may include further comprising synthesizing an RNA by means of an RNA polymerase or including an RNA polymerase in the reaction mixture for synthesizing RNA.

The RNA for use in the method may be obtained from a biological sample and may in one or more examples include an RNA molecule of the following type: messenger RNA, transfer RNA, ribosomal RNA, microRNA, long non coding RNA, antisense RNA, CRISPR RNA, Piwi interacting RNA, small interfering RNAs, 7SK RNA, enhancer RNA, spliced leader RNA, telomerase RNA component, guide RNA, small nuclear RNA, small nucleolar RNA, ectosomal RNA, and viral RNA.

In general, a kit may be provided that contains a reaction vessel for receiving a sample suspected of containing an RNase, the reaction vessel containing the composition according to claim 1 that is either immobilized or in solution or dried suitable for receiving a sample containing a target RNA. Examples of a suitable RNase inhibitor are described above and include one or more oligonucleotides having a sequence with at least 90% identity to any of the sequences selected from SEQ ID NOs: 1-62.

BRIEF DESCRIPTION OF FIGURES

FIG. 1 shows 61 examples of aptamer sequences that were selected for their binding to RNases and for inhibiting RNase activity.

FIG. 3A-3H shows that aptamers that bind to RNase A or RNase I, when combined in a mixture, efficiently inhibit both RNase A and RNase I. Inhibition of RNA degradation by this mixture of RNases is greater than observed with commercial products when the commercial products are used at 2 fold greater concentrations than recommended by the respective manufacturers (RNasin from Promega and SUPERase-In from ThermoFisher).

FIG. 3A shows complete loss of RNA in the absence of an RNA inhibitor.

FIG. 3B shows substrate digestion in the presence of an aptamer that inhibits RNase A only.

FIG. 3C shows substrate digestion in the presence of an aptamer that inhibits RNase I only.

FIG. 3D shows substrate digestion in the presence of Murine inhibitor that inhibits RNase A only.

FIG. 3E shows substrate digestion in the presence of RNasin (Promega) that inhibits RNase A only.

FIG. 3F shows substrate digestion in the presence of SUPERase-In (ThermoFisher) that is designed to inhibit RNase A and RNase I.

FIG. 3G shows significantly reduced substrate digestion when both aptamer to RNase I and Murine Inhibitor (New England Biolabs, Ipswich, MA) are used together.

FIG. 3H shows much enhanced protection against substrate digestion by RNase A and RNase I by a mixture of aptamers compared to the individual protection by two commercial aptamers shown in FIGS. 3E-3F against RNase A or RNase I, respectively.

Lane 1: Intact RNA.

Lane 2: 25% urine or urine pre-treated RNA samples containing aptamer.

Lane 3: Biotin aptamer with increasing amounts of streptavidin-functionalized beads showing that functionalization with biotin did not affect aptamer performance (compare Lane 3 with Lane 2).

Lane 4: is a control with RNA in a urine sample but no aptamer (degraded RNA).

Lane 5-8: Beads (% v/v) added to sample in the absence of aptamer at varying concentrations.

Lane 9-12: Beads bound with biotinylated aptamer showing preservation of intact RNA.

Figure 5:
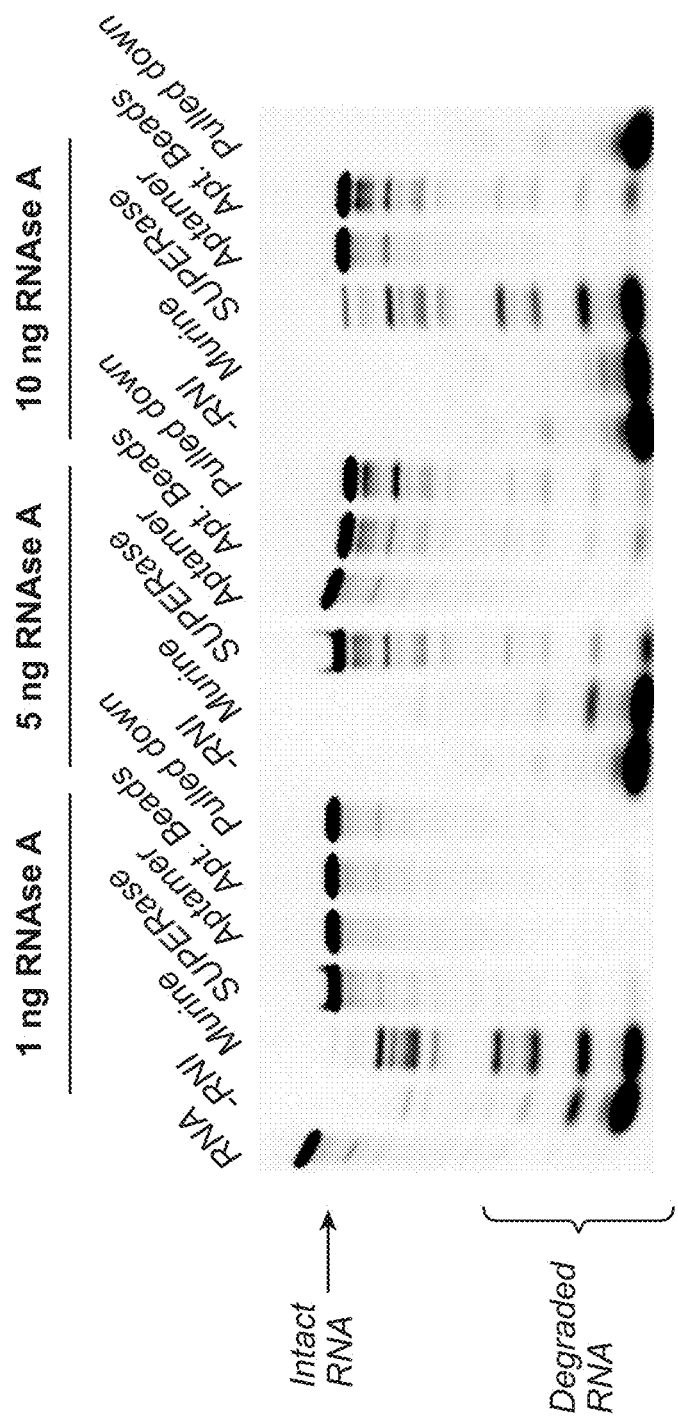

FIG. 5 shows that a single concentration of aptamer or aptamer coated beads protected RNA from digestion in the presence of increasing concentrations of RNase A (1 ng, 5 ng and 10 ng) more effectively than any commercial protein-based alternative used at double the recommended concentrations.

Lane 1 is intact RNA only.

Lanes 2-7 show the effect of RNase inhibitors in the presence of 1 ng RNase.

Lane 2 is RNase inhibitor only.

Lane 3 is Murine RNase inhibitor.

Lane 4 is SUPERase-In from ThermoFisher.

Lane 5 is an aptamer.

Lane 6 is aptamer beads added to the RNA before RNase but not pulled down; and

Lane 7 is aptamer beads that interact with RNase A and are pulled down before the supernatant is assayed for RNA.

Lanes 8-13 same as Lanes 2-7 but with 5 ng RNase A.

Lanes 14-20 same as Lanes 2-7 but with 10 ng RNase A.

Figure 6A:
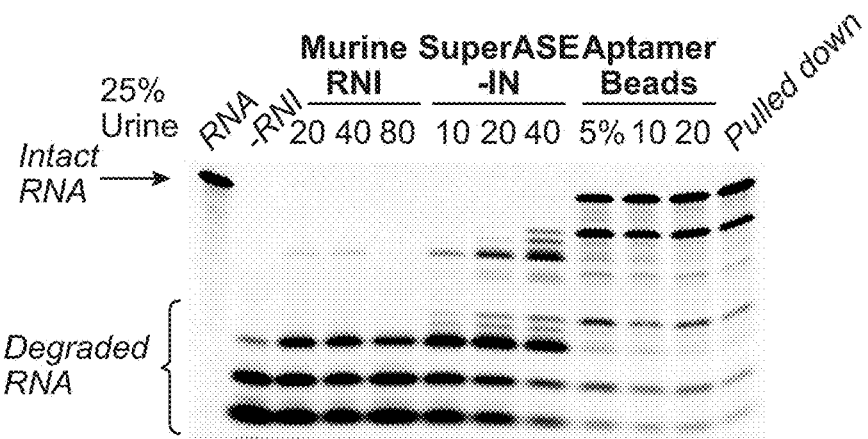
Figure 6B:
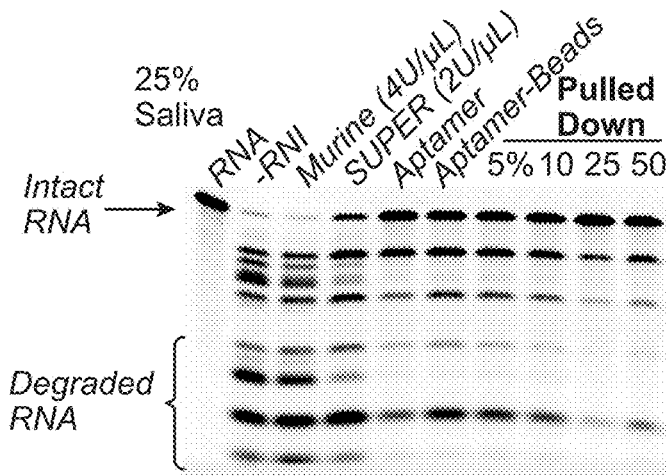
Figure 6C:
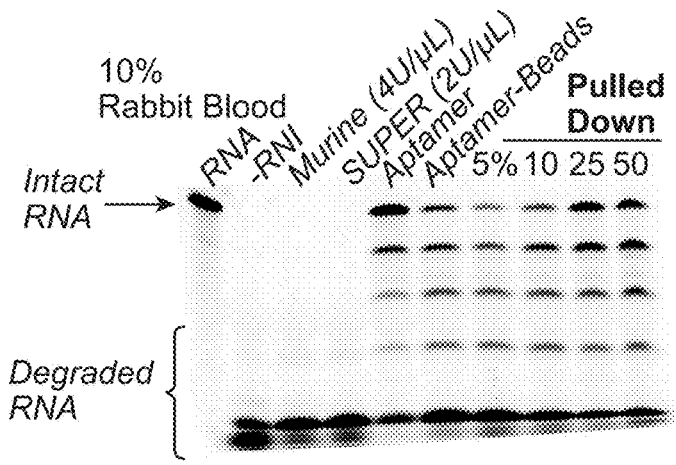

FIG. 6A-6C show that aptamers are more effective in protecting RNA against RNase degradation in 25% urine, 25% saliva and 10% blood than protein inhibitors.

FIG. 6A shows how intact RNA is preserved in 25% urine when RNase inhibitor aptamer coated beads are provided at a v/v concentration of 5%, 10% and 20% to pull down RNase from urine before the urine is added to the RNA. In contrast, the RNA is degraded in the presence of SUPERase-In and Murine RNI under manufacturer's recommended concentrations. Lane 1 is the intact RNA control, Lane 2 is RNA inhibitor control, Lanes 3-5 show increasing concentrations of Murine inhibitor (20 ng, 40 ng and 80 ng), Lanes 6-8 show increasing concentrations of SUPERase-In (10 ng, 20 ng and 40 ng), Lanes 9-12 show increasing amounts of aptamer beads (5%, 10% and 20% v/v) while lane 13 show urine after a treatment with beads and pull-down before adding urine to reaction.

FIG. 6B shows how intact RNA is preserved in 25% saliva when RNase inhibitor aptamer coated beads are provided at a v/v concentration of 5%, 10% and 20% to pull down RNase in 25% saliva before the saliva is added to the RNA. Aptamer added directly to the 25% saliva and aptamer coated beads added directly to the saliva both then added to RNA were substantially similarly effective. In contrast, the RNA is degraded in the presence of SUPERase-In and Murine ribonuclease inhibitors (RNI) under manufacturer's recommended concentrations.

FIG. 6C shows how a portion of intact RNA is preserved in 10% blood when RNase inhibitor aptamer coated beads are provided at a v/v concentration of 25% and 50% to pull down RNase in 10% blood (v/v) in buffer before the blood preparation is added to the RNA. A portion of intact RNA is also preserved in the presence of aptamer or aptamer coated beads combined with 10% blood and RNA. In contrast, the RNA is completely degraded in the presence of SUPERase-IN and Murine ribonuclease inhibitors (RNI) under manufacturer's recommended concentrations.

Figure 7A:
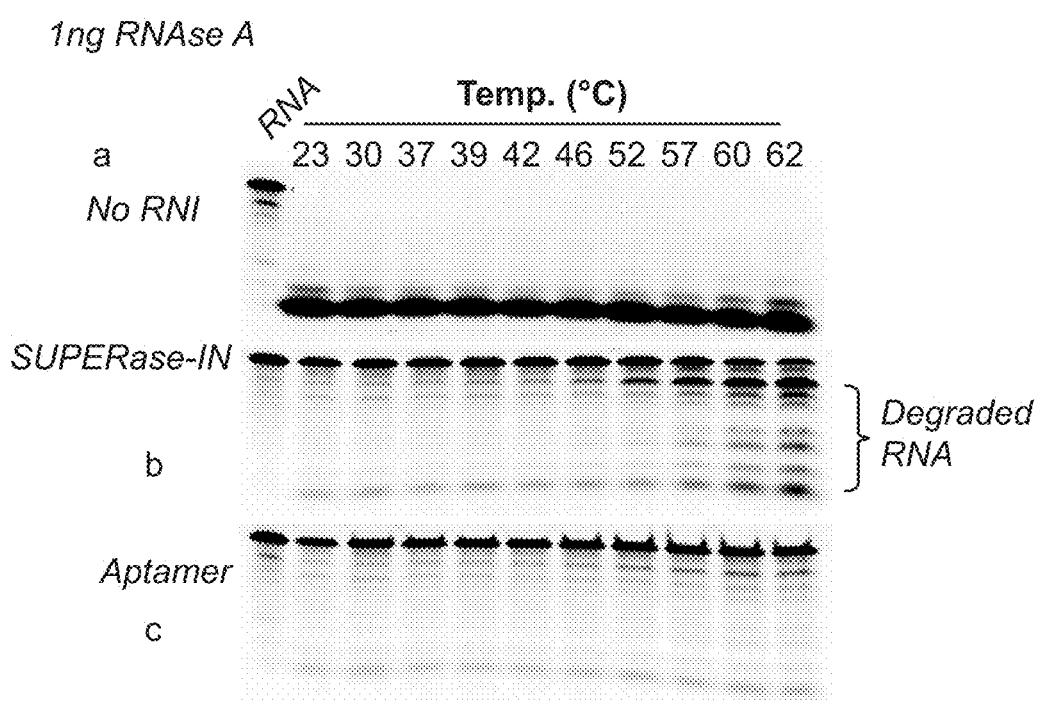
Figure 7B:
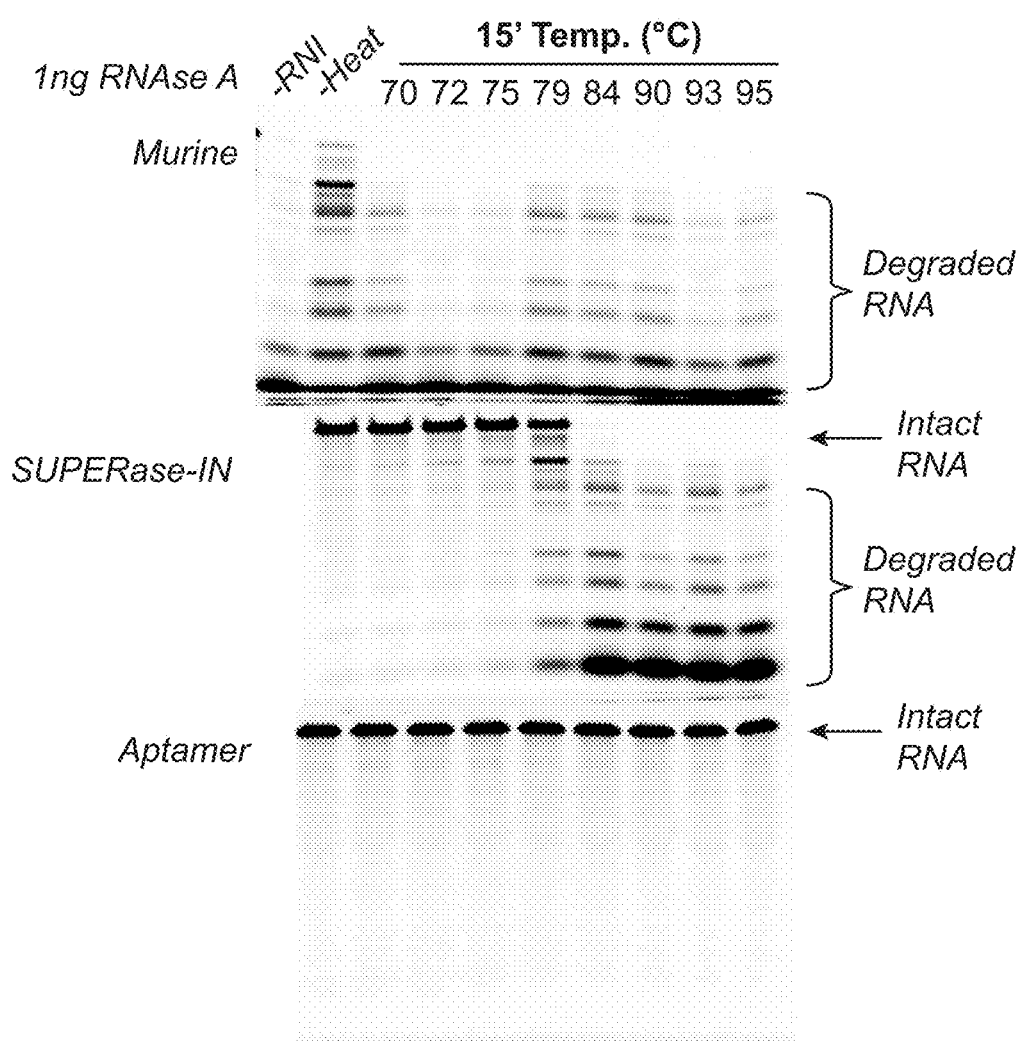

FIG. 7A-7B shows that the aptamer inhibition of RNase is more effective in protecting RNA when tested in the range of 23° C.-95° C. than protein inhibitors. SUPERase-IN (protein) has reduced inhibitory activity at 46° C. and decreases as the temperature is increased to 62° C. A control was provided of RNase A in the absence of an inhibitor.

FIG. 7A shows that the aptamer is an effective inhibitor of RNase A at temperatures between 23° C.-62° C. The results of varying the temperature from 23° C. to 62° C. on RNA are shown in (a) for no RNA inhibitor (b) for SUPERase-In and (c) for aptamer.

FIG. 7B shows that the aptamer RNase inhibitor is more thermostable than protein RNase inhibitors. The results of pretreatment for 15 minutes at temperatures of 70° C.-95° C. is shown in (a) for no RNase inhibitor (b) for SUPERase-In and (c) for aptamer.

Figure 8A:
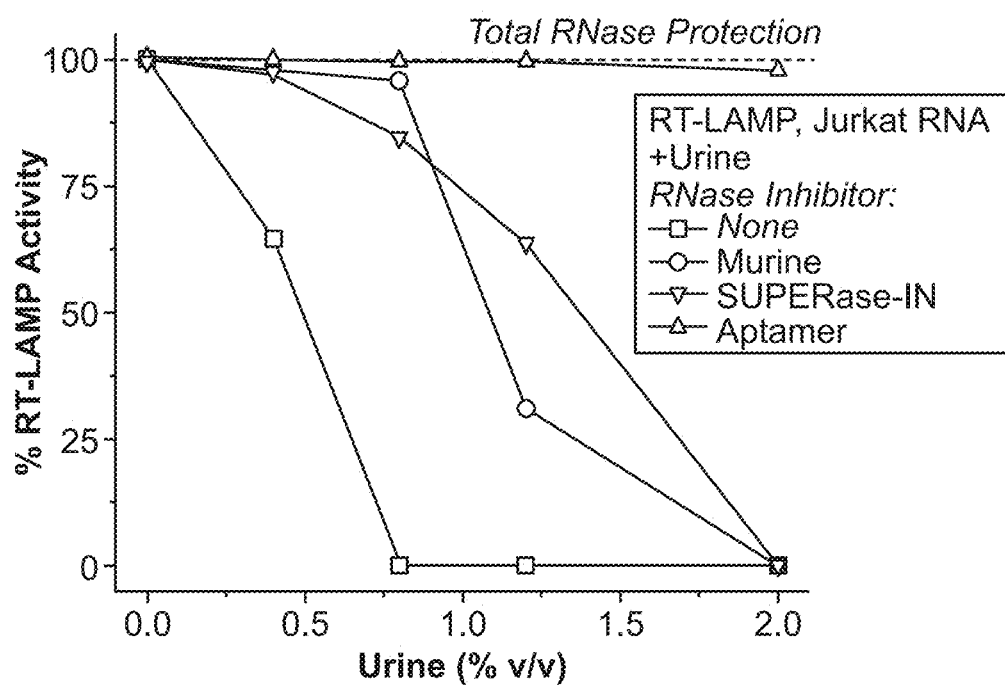
Figure 8B:
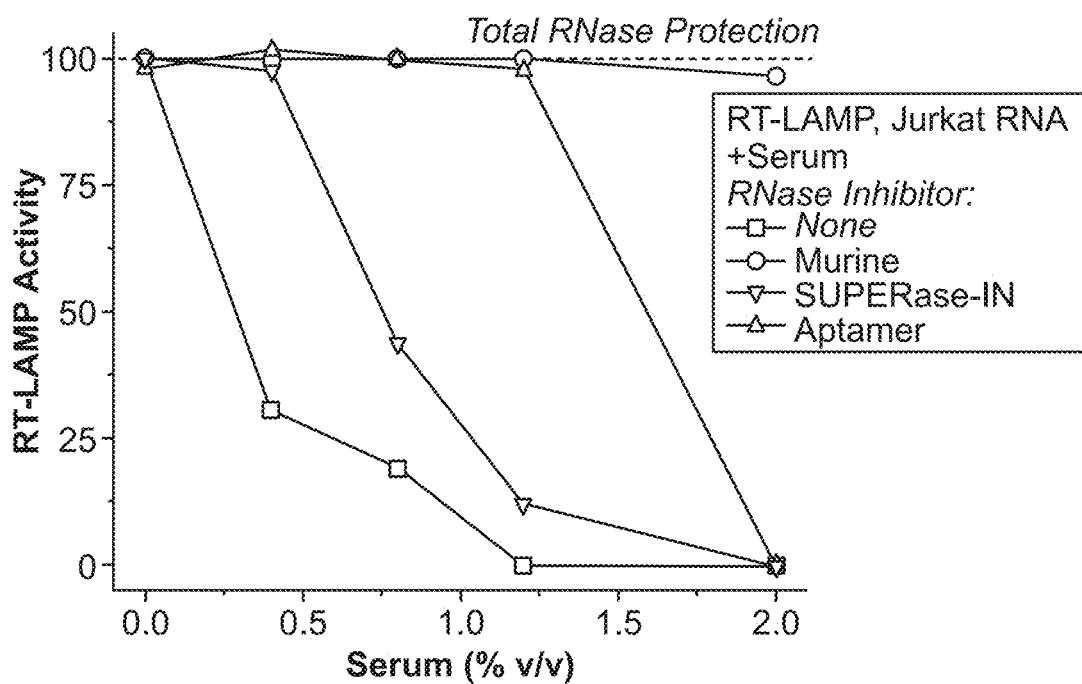

FIG. 8A and FIG. 8B shows that substantially 100% of the RNA is protected from RNA degradation by the aptamer in the presence of a biological fluid. The results of amplification (LAMP) of human ACTB in total Jurkat RNA in the presence of urine or serum is shown. The % RT-LAMP activity is represented on the Y-axis and the concentration of biological fluid is represented on the X-axis.

FIG. 8A shows that substantially 100% of the RNA is protected from RNase degradation by the aptamer in 2% urine whereas the RNA is totally degraded by RNase in 2% urine in the presence of SUPERase-In and Murine inhibitor.

FIG. 8B shows that substantially 100% of the RNA is protected from RNase degradation by the aptamer and the Murine inhibitor in 1.2% serum whereas the RNA whereas about 95% of the RNA is totally degraded by RNase in 1.2% serum in the presence of SUPERase-In.

FIG. 9A-9D show that the amount of RNA product is maintained without significant degradation in the presence of aptamer. RNase A or RNase I concentrations are increased in 2 fold steps from 2 pg-1 ng concentrations in the presence of 1 μM aptamer.

Figure 9A:
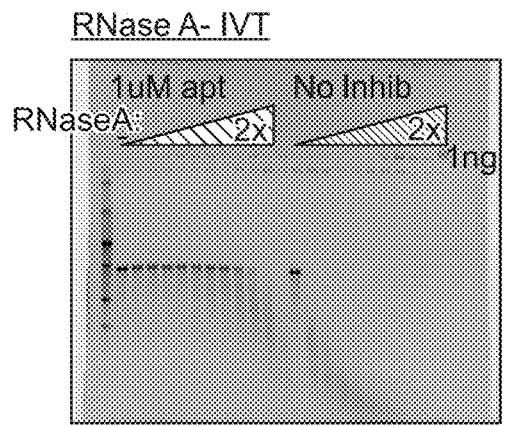

FIG. 9A compares the amount of intact RNA on a gel +/−1 μM aptamer in the presence of increasing amounts of RNase A.

Figure 9C:
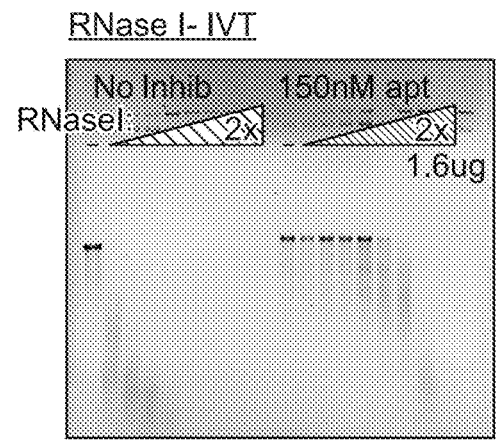
Figure 9B:
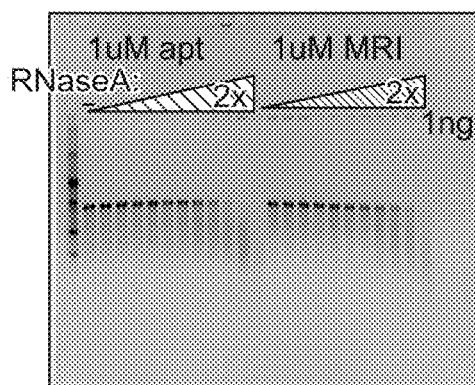

FIG. 9B compares the amount of intact RNA on a gel +/−1 μM Murine inhibitor in the presence of increasing amounts of RNase A.

FIG. 9C compares the amount of intact RNA on a gel +/−150 nM aptamer in the presence of increasing amounts of RNase A.

Figure 9D:
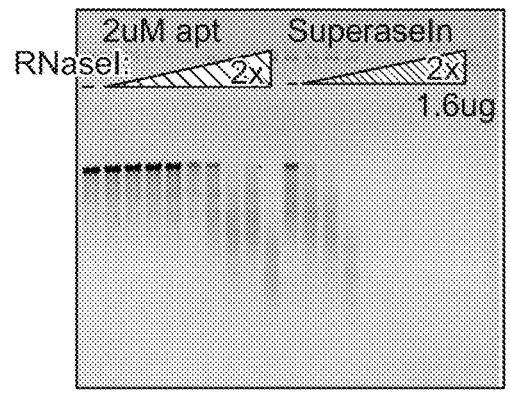

FIG. 9D compares the amount of intact RNA on a gel +2 μM aptamer or 1.6 pg SUPERase-In in the presence of increasing amounts of RNase A.

FIGS. 1DA-10C show that while RT-qPCR and IVT are prevented by RNase A/I activity the adverse effect of the RNase inhibitor is reversed in the presence of aptamer. The aptamer is shown not interfere with RT-qPCR. The amount of DNA product from RT-qPCR was analyzed in the presence of aptamer compared with in the absence of aptamer where an increase in cycles is inversely correlated to the amount of template for amplification.

Figure 10A:
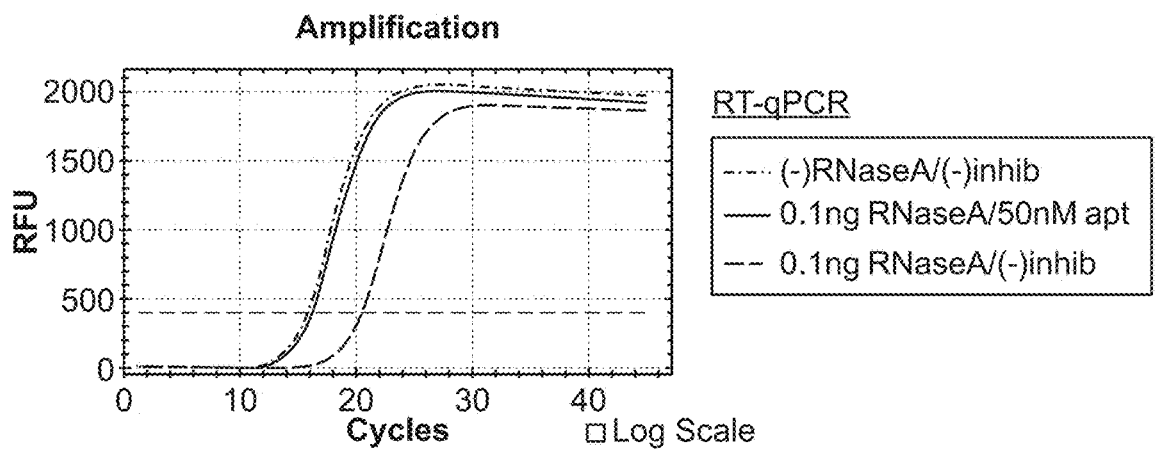

FIG. 10A shows that free aptamer (50 nM) added to a DNA in an in vitro transcription reaction in the presence of 0.1 ng RNase A produces more intact RNA than in the absence of inhibitor.

Figure 10B:
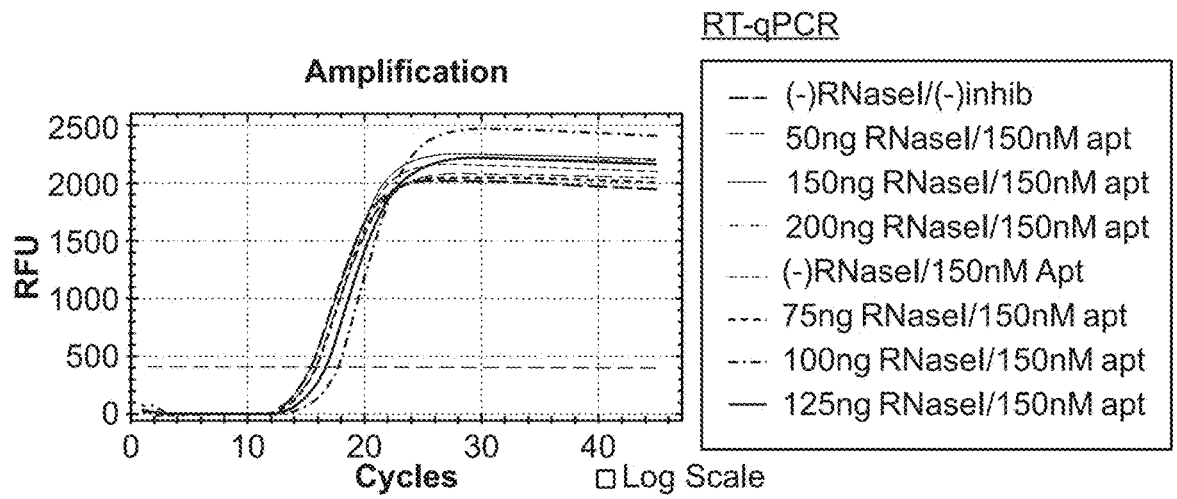

FIG. 10B shows that free aptamer (150 nM) added to a DNA in an in vitro transcription reaction in the presence of 50 ng, 75 ng, 100 ng and 150 ng and 200 ng RNase I produces more intact RNA than in the absence of inhibitor. Murine inhibitor is inactive against RNase I.

DETAILED DESCRIPTION OF EMBODIMENTS

Provided herein is a solution to inhibiting RNases. RNases are found everywhere in the environment and in the laboratory. RNases compromise and degrade RNA populations that are targeted for study or use as research, diagnostic and/or therapeutic agents. RNase Inhibitors are molecules that prevent one or more types of RNase from degrading RNA. Compositions and methods provided herein can target a plurality of RNases from different sources. RNases may vary according to their sources. For example, RNases found in bacteria and in many prokaryotes are identified as RNase I whereas those from mammals, more generally Eukaryotes, are identified as RNase A. These RNases may be transmitted by users during laboratory manipulations on purified RNA. This may occur from contamination directly from the laboratory technician or may occur when the RNase is a contaminant in reagents applied to RNA in the laboratory. A major source of RNase is from the biological environments from which the RNAs are obtained and/or purified. The degradation of target RNAs by RNases is a major problem in RNA biology. Degradation by these enzymes cause wasteful loss of purified material and misrepresentation of RNA species in a population, for example, gene expression profiling, where certain rarer species of RNA fall below the threshold of detectability. Moreover, RNases are abundant in the environment so that RNase inhibitors should be efficient, readily available and cost effective. RNases are very robust enzymes that can withstand temperatures as high as 60° C. or higher and significant pH fluctuations.

Commercial inhibitors based on proteins are problematic for reasons that include cost, efficacy, long term shelf life and carry-over of RNases associated with their manufacture. Chemically synthesized oligonucleotide aptamers described herein have advantages over existing RNase inhibitors in features that include one or more of the following: cost of manufacture, supply, efficacy, long shelf life and tolerance to high temperatures. In some embodiments, the chemically synthesized oligonucleotide aptamers selected as RNase inhibitors can be optionally modified by hydrophobic groups on one or more nucleotides to enhance inhibitory binding of the oligonucleotide to the RNase. Examples of hydrophobic groups are provided in FIG. 14 of U.S. Pat. No. 8,975,388 calling out in particular 5-(N-benzylcarboxyamide)-dUTP (BndUTP), 5-(N-isobutylcarboxyamide)-dUTP (iBudUTP), or 5-(N-tryptaminocarboxyamide)-dUTP (Trp dUTP) and including Napthyl-dU for increasing dissociation half-life of aptamers.

Moreover, aptamer RNase inhibitors may be readily immobilized on an appropriate substrate. For example, aptamer RNase inhibitors may be immobilized on beads such as magnetic beads. Such aptamer bound magnetic beads may be added to an isolate of biological material for RNA analysis or to a preparation of partially or completely purified RNA. The magnetic beads with bound material may be readily removed from preparations by exposing the reaction vessel to a magnet and removing unbound material. Other types of aptamer RNase inhibitor immobilization substrates include plastic dishes such as microwell plastic plates or other reaction vessels. Here the RNase inhibitor may be bound directly to the surface of the microwell plastic plates or other reaction vessel to enable binding and inhibition of RNase and its removal from the RNA containing mixture.

An embodiment of the present methods is to utilize aptamer RNase inhibitors in a reaction container into which a swab, or biological fluid such as a nasal or mouth wash, blood, serum, saliva, sputum, mucosal secretions, sweat, wax or other fluid is added from a patient for a diagnostic test to test for RNA either for gene expression profiling or for pathogen detection such as RNA virus detection. Accordingly, the aptamer may be immobilized in the reaction container, present in solution or in dried form (e.g., lyophilized or dried) for inhibiting RNase activity when a sample is added to the reaction container to permit RNA analysis without significant loss of the RNA sample. Optionally, a Proteinase K may additionally be added either immobilized, in solution, dried or lyophilized with the aptamer for digesting protein in the biological sample to increase the availability of an RNA of interest. An example of a proteinase is Proteinase K, for example, a thermostable Proteinase K (U.S. Pat. No. 10,633,644). The available RNA may be analyzed by means of a reverse transcriptase and/or amplification using any amplification technique known in the art such as LAMP, SDA, PCR etc. (see for example, U.S. Pat. No. 9,580,748).

RNA Synthesis reactions are vulnerable to RNase contamination. The present RNase inhibitors are preferably compatible with biological agents used in RNA synthesis such as for example, an RNA polymerase and a vaccinia capping enzyme or other capping enzyme, a polyA polymerase, and/or a reverse transcriptase. The RNase inhibitor is also preferably compatible with non-biological agents used in RNA synthesis such as nucleoside triphosphates, RNA synthesis temperatures used for effective periods of time. The RNase inhibitor is also preferably compatible with downstream reactions such as DNA amplification discussed above which may contain reversible oligonucleotide inhibitors of DNA polymerases and reverse transcriptases. The RNase inhibitors should further have a satisfactory storage shelf life of at least months if not a year or more in a suitable storage buffer.

The term "biological sample" refers to any material that contains nucleic acid including plant matter, soil, waste material, animal material, pathogens, pathogen vectors, microorganisms etc. Biological samples include enzyme reagents used in RNA reactions.

The phrase "biological fluid derived from an animal body" includes a fluid selected from one or more of the following: urine, blood, serum, saliva, sputum, mucosal secretions, sweat, wax or other fluid from a body where the term "animal" refers to human, mammal or any multicellular organism.

The phrase "the biological sample derived from an environmental sample" includes a sample selected from one or more of the following; water from rivers, streams, the sea; sludge, swamp or air.

The term "target RNA" refers to any RNA of interest in a research, diagnostic or therapeutic context.

Populations of RNA also referred to as "RNA" include messenger RNA, transfer RNA, ribosomal RNA, microRNA, long non coding RNA, antisense RNA, CRISPR RNA, Piwi interacting RNA, small interfering RNAs, 7SK RNA, enhancer RNA, spliced leader RNA, telomerase RNA component, guide RNA, small nuclear RNA, small nucleolar RNA, ectosomal RNA, and viral RNA.

The term "aptamer" as used herein refers to a oligonucleotide typically single stranded and having a length of 20-100 nucleotides, for example, 30-100 nucleotides, or for example 40-80 nucleotides. An aptamer can bind to a protein to inhibit its activity. In general, aptamers are selected to bind a protein to inhibit its activity under certain reversible conditions so that when those conditions change, the aptamer is released and the protein becomes active. In embodiments of the invention, the aptamer is designed to bind to an RNase and to remain bound under common experimental conditions that include raised temperatures utilized during reverse transcription that is preferentially executed in the absence of RNase activity. In one embodiment, the RNase inhibitor preferably does not release the RNase under any reaction condition used for synthesizing RNA or studying intact RNA.

Examples of RNase inhibitors that meet the criteria described above for use in: RNA synthetic reactions and that are compatible with downstream reactions such as reverse transcribing the RNA, sequencing RNA directly; RNA reagents such as RNA guides in cleavage reactions (for example, CrispR or Argonaut reactions), ribozymes etc.; analysis of RNA in the environment such as microRNAs, long non-coding RNAs, transcribed RNA, transcriptomes etc., and any reaction for which degradation of RNA by RNases is undesirable; are oligonucleotides having a sequence with at least 90%, 91%, 92%, 93%, 94%, 95%, 96%, 97%, 98%, 99% or 100% sequence identity to at least one of SEQ ID NOs: 1-62. Examples of RNase inhibitors having sequences selected from those of at least 90% identity to SEQ ID NOs: 1-62 are those with at least 90% identity to at least one sequence selected from SEQ ID NOs: 1-31 for RNase A inhibition, for example SEQ ID NO:10 or 21 and those with at least 90% identity to at least one sequence selected from SEQ ID NOs: 31-61 for example SEQ ID NOs: 31-45 for inhibitors of RNase I. RNase inhibitors having a consensus sequence of at least 90% identity with SEQ ID NO: 62 are exemplified by SEQ ID NOs:29 and 31 where R in the consensus sequence is represented by A or G in SEQ ID NOs: 29 and 31.

In embodiments of the compositions and methods, the RNase inhibitor is stable at temperatures of at least up to 90° C. The RNase inhibitor is also preferably stable at temperatures below 30° C. for example below 20° C., below 10° C. and below 0° C. The inhibitors are preferably stable for at least 5 minutes at any selected temperature for example, at least 15 minutes, 30 minutes, 40 minutes or 60 minutes selected to inhibit RNase in a biological sample. In embodiments, the RNase inhibitor is preferably stable and suitable for storage for at least 1 month, 3 months, 6 months or 12 months at room temperature (about 27° C.) either in a buffer, dried, lyophilized or immobilized on a matrix such as beads or plastic.

In an embodiment of the composition and methods, the RNase inhibitor is capable of inhibiting at least 80%, at last 90%, or at least 95% of the RNase activity (RNase A and/or RNase I activity) at a selected temperature and time as exemplified above. Other RNase types in addition to RNase A and/or RNase I) may also be inhibited and a mixture of RNase inhibitors may be combined to this end.

Unless otherwise defined, all technical and scientific terms used herein have the same meaning as commonly understood by one of ordinary skill in the art to which this disclosure belongs. Still, certain elements may be defined for the sake of clarity and ease of reference. It is also to be understood that the terminology used herein is for the purpose of describing particular embodiments only, and is not intended to be limiting, since the scope of the present teachings will be limited only by the appended claims.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular Biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a", "an", and "the" include plural referents unless the context clearly dictates otherwise. For example, the term "a protein" refers to one or more protein, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Aspects of the present disclosure can be further understood in light of the embodiments, section headings, figures, descriptions and examples, none of which should be construed as limiting the scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Numeric ranges are inclusive of the numbers defining the range. When sample numerical values are provided, they may represent, unless specified otherwise, an intermediate value in a range of values.

The term "non-naturally occurring" as used herein refers to a composition that does not exist in nature.

In the context of a nucleic acid, the term "non-naturally occurring" refers to a nucleic acid that contains: (a) a sequence of nucleotides that is different from a nucleic acid in its natural state (i.e., having less than 100% sequence identity to a naturally occurring nucleic acid sequence); (b) one or more non-naturally occurring nucleotide monomers (which may result in a non-natural backbone or sugar that is not G, A, T or C); and/or C) may contain one or more other modifications (e.g., an added label or other moiety) to the 5'-end, the 3' end, and/or between the 5'- and 3'-ends of the nucleic acid.

In the context of a composition, the term "non-naturally occurring" refers to: (a) a combination of components that are not combined by nature, e.g., because they are at different locations, in different cells or different cell compartments; (b) a combination of components that have relative concentrations that are not found in nature; (c) a combination that lacks something that is usually associated with one of the components in nature; (d) a combination that is in a form that is not found in nature, e.g., dried, freeze dried, crystalline, aqueous; and/or (e) a combination that contains a component that is not found in nature. For example, a composition may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature. The non-naturally occurring polymerase may be purified so that it does not contain DNases, RNases or other proteins with undesirable enzyme activity or undesirable small molecules that could adversely affect the sample substrate or reaction kinetics.

All publications, patents, and patent applications mentioned in this specification are herein incorporated by reference to the same extent as if each individual publication, patent, or patent application was specifically and individually indicated to be incorporated by reference including U.S. Provisional Application Serial Nos. 62/992,921 and 63/001,417.

EXAMPLES

Example 1: Selection of Aptamers that Inhibit RNases Using Systematic Evolution of Ligands by Exponential Enrichment (SELEX) and Suitable Assays SELEX Selection Aptamers were selected using systematic evolution of ligands by exponential enrichment (SELEX). This method has been widely used for example, to obtain reversible inhibitors of DNA polymerase reagents. The method has also been used widely to reversibly bind various cell proteins in the study of phenotypes and as potential therapeutic agents (e.g., Tuerk, et al (1990), Science 249 p 505-10; Blackwell, et al. (1990) Science 250 1104-10, Gold et al. 2010. PLoS ONE vol 5; Stoltenburg, et al. (2015) PLOS ONE vol 10; Wu, et al (2016), Methods 106, 21-28). The single strand oligonucleotide inhibitors selected for inhibition of RNase A and RNase I are shown in FIG. 1. A consensus sequence for the RNase inhibitor is 5'-TTCGAATGCATTTCGAACATCTRTATCARC-3' (SEQ ID NO: 62) where R=A or G where the consensus sequence was found to be a particularly potent consensus sequence for aptamer inhibitors of RNase A.

Figure 2:
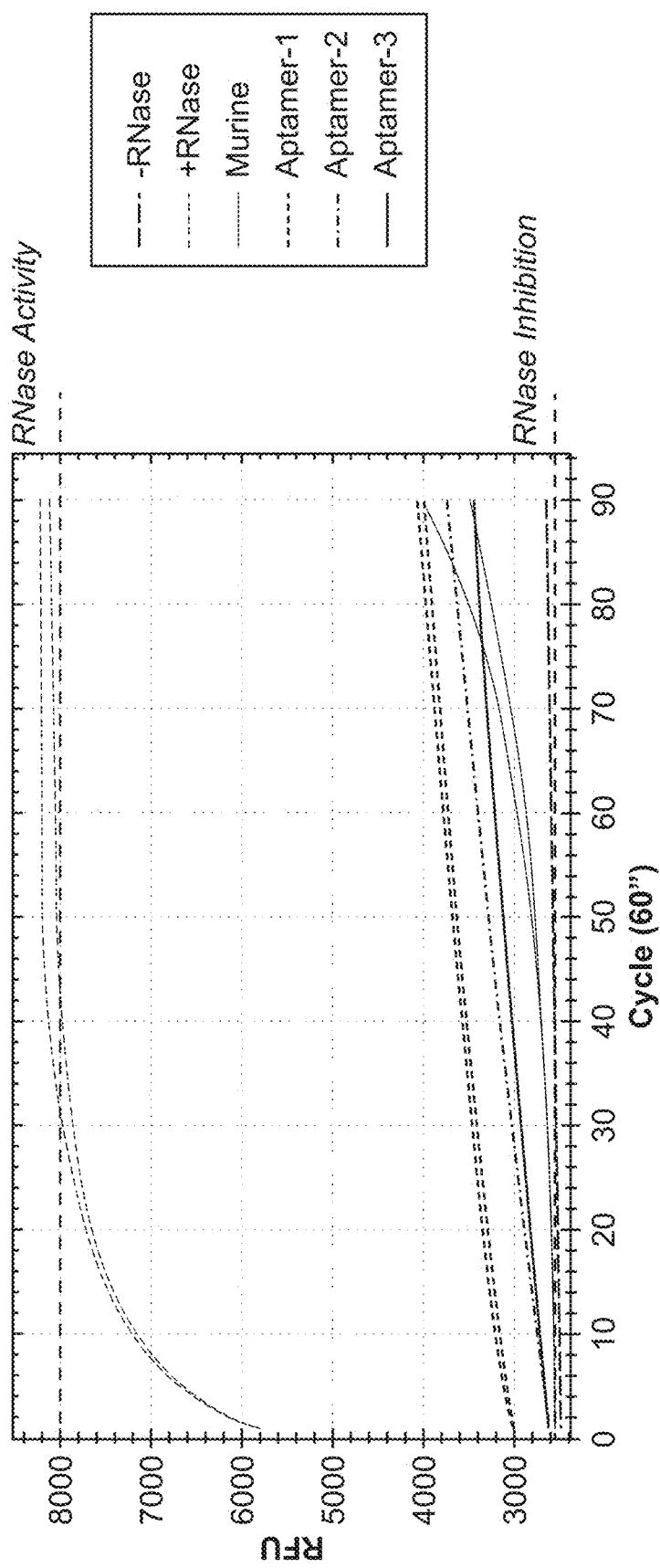
FIG. 2 shows examples of three of the RNase A nucleic acid aptamers demonstrating that RNase A digestion of a preparation of 33 base synthetic RNAs (RNA library is RNaseAlert® from Integrated DNA Technologies (Coralville, Iowa) is inhibited by each of the aptamers at least as effectively as the Murine protein RNase Inhibitor (New England Biolabs, Ipswich, MA). The black solid line is the control (no RNase).

Assay for Aptamer Inhibition of RNases 0.2 mM RNaseAlert RNA substrate (33 bases), containing a fluorophore reporter on one end and a quencher on the other (ThermoFisher, Waltham, MA), was incubated with 100 pg (0.4 nM) RNase A with or without 8 nM RNase A inhibitor at 37° C. for 90 minutes with fluorescent readings every 60 seconds (each 60 second interval noted on x-axis). Digestion of RNA by RNase A results in the separation of fluorophore and quencher, producing a rise in fluorescent signal (+RNase red trace). Three RNase A aptamers and Murine RNase Inhibitor are able to inhibit RNA digestion, but Murine Inhibitor show a slows a loss in RNase inhibition over time (see FIG. 2).

Example 2: Inhibition of RNase A and RNase I in a Sample was Achieved by Adding a Mixture of 2 Aptamers with Different Specificities Using the assay described in Example 1, various concentrations of indicated RNase inhibitors (100 μM RNase A aptamer, 150 μM RNase I aptamer, 1 U Murine inhibitor, 1U RNasin, 1U SUPERase-In and RNA were added to various amounts of an RNase A/RNase I mixture (six 4-fold serial dilutions starting at 1 ng RNase A+50 ng RNase I) and incubated at 37° C. for 120 minutes. Fluorescent readings were taken every 60 seconds with each X-axis interval representing one 60 second cycle. Digestion of RNA was measured by fluorescence reading (RFU). None of the RNase inhibitors, as stand-alone inhibitors, was able to prevent substrate digestion from the RNase cocktail. Only the inhibitor mixtures containing two aptamers, were able to efficiently inhibit RNA digestion (see FIG. 3G-3H).

Example 3: Aptamers Bound to Beads were as Effective at Inhibiting RNases as were Aptamers Alone 10 pmol of FAM-labeled RNaseAlert RNA substrate (33 bases) was incubated for 15 minutes at 25° C. in the presence of 25% urine or urine pre-treated with increasing amount of streptavidin-functionalized beads. Beads were either washed with buffer and no RNase A aptamer or bound with biotinylated RNase A aptamer. Functionalization with biotin did not affect aptamer performance and only beads bound by biotinylated aptamer were able to reduce RNase activity. Urine pre-treatment was performed by incubating urine with increasing amounts of beads for 10 minutes at room temperature with agitation, then pulling beads down with magnet and transferring supernatant for use in reactions.

Figure 4:
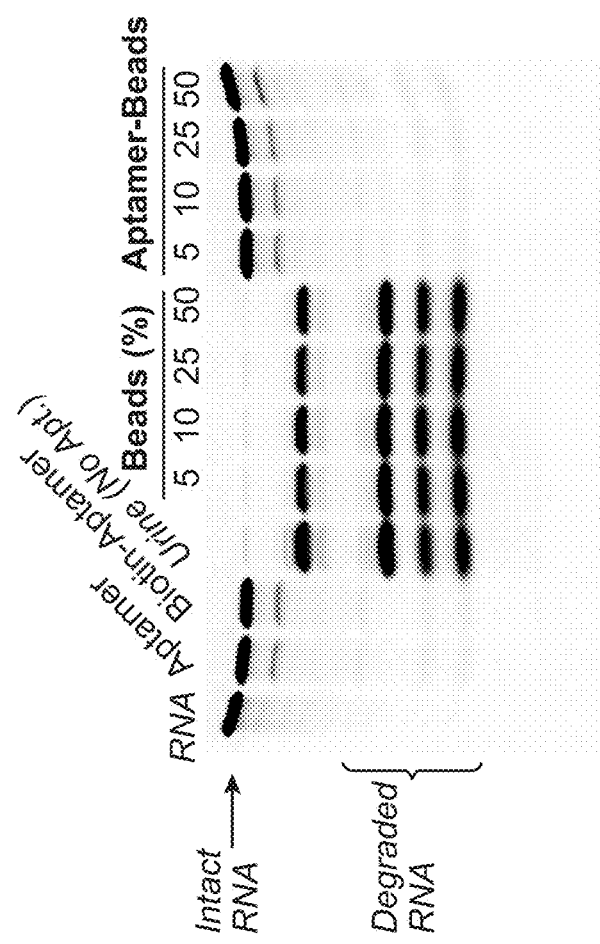
FIG. 4 shows that RNA remains intact in urine in the presence of aptamers that inhibit RNase A where the aptamers are either free in solution, or biotinylated and coated on magnetic beads. Where aptamer coated beads were used, the RNase inhibition was shown to be due only to the aptamer and not to the beads in the absence of aptamer.

Streptavidin beads were bound to biotinylated aptamer using manufacturer recommended protocol (New England Biolabs, Ipswich, MA). Products were analyzed by electrophoresis on 20% TBE gel and imaged using ChemiDoc™ MP (Bio-Rad, Hercules, CA) with fluorescein settings (see FIG. 4).

Example 4: Aptamers are More Efficient Inhibitors of Rnase Activity than Protein Inhibitors 10 pmol of FAM-labeled RNaseAlert RNA substrate (33 bases) was incubated for 15 minutes at 25° C. in the presence of 1, 5, or 10 ng RNase A and RNase Inhibitor as indicated.

Murine RNase Inhibitor (4 U/μL) offered some protection of RNA with 1 ng RNase A but not higher amounts of RNase A, and SUPERase-IN (2 U/μL,) was able to protect with 5 ng RNase A but not higher. 10 μM aptamer completely inhibited even 10 ng RNase A, as did 25% v/v aptamer-functionalized beads. RNase A solutions were pre-treated by incubating 1, 5, or 10 ng/μL RNase A with 25% v/v beads for 10 minutes at room temperature with agitation, then pulling beads down with magnet and transferring supernatant for use in reactions. Pulldown was insufficient to offer protection from 10 ng RNase A solution but worked for lower concentrations. Streptavidin beads were bound to biotinylated aptamer using manufacturer recommended protocol. Products were analyzed by electrophoresis on 20% TBE gel and imaged using Bio-Rad ChemiDoc MP with fluorescein settings (see FIG. 5).

Example 5: Aptamers Inhibit Rnases in Biological Samples in Addition to Rnases in Purified RNA 10 pmol of FAM-labeled RNaseAlert RNA substrate (33 bases) was incubated for 15 minutes at 25° C. in the presence of 25% v/v urine, 25% v/v saliva, or 10% rabbit blood v/v and Murine RNase Inhibitor (2, 4, 8 U/μL), SUPERase-IN (1, 2, 4 U/μL) or aptamer beads (5%, 10% or 20% v/v). Products were analyzed by electrophoresis on 20% TBE gel (see FIGS. 6A-6C and imaged using Bio-Rad ChemiDoc MP with fluorescein settings).

Aptamer beads were assembled using biotinylated aptamer bound to Streptavidin coated beads. For pulldown, whole urine, saliva, or blood were pre-treated by incubation with aptamer beads for 10 minutes at room temperature with agitation, then the beads were removed with a magnet and the supernatant was transferred to another reaction tube for further reactions.

The results are shown in FIG. 6A-6C. Murine RNase Inhibitor (2, 4, 8 U/μL) and SUPERase-IN (1, 2, 4 U/μL) offered slight protection of RNA in urine and saliva, but no full-length RNA was preserved in Rabbit Blood. In contrast the aptamer and immobilized aptamer preserved >50% full length RNA in all 3 biological fluids, whether added at reaction time or after pretreatment with beads in an RNase A pull down reaction.

Example 6: Aptamers are Stable in a Wide Range of Temperatures

A. Heat Stability of aptamers—heat treatment during inhibition reaction.

10 pmol of FAM-labeled RNaseAlert RNA substrate (33 bases) was incubated for 15 minutes at the indicated temperature in a 10 μL reaction with 1 ng RNase A. Products were analyzed by electrophoresis on 20% TBE gel and imaged using Bio-Rad ChemiDoc MP with fluorescein settings.

RNase A completely degraded the RNA at all temperatures, but was inhibited efficiently by both inhibitors (SUPERase-IN and Aptamer) up to temperatures of about 50° C. At higher temperatures, SUPERase-IN provided less than 50% inhibition at 60° C. while the aptamer substantially maintained total inhibition of RNA degradation at 60° C. (See FIG. 7A-7B).

B. Heat stability and retention of inhibitory activity of aptamers after pretreatment of aptamers at temperatures in the range 70° C.-95° C.

10 pmol of FAM-labeled 33b RNA was incubated for 15 minutes at the indicated temperature in a 10 μL reaction with 1 ng RNase A. Reactions contained Murine RNase inhibition (8 U/μL, top), SUPERase-IN (4 U/μL, middle), or aptamer (10 μM) with the inhibitor being pre-treated by heating for 15 minutes at the indicated temperature. Products were analyzed by electrophoresis on 20% TBE gel and imaged using Bio-Rad ChemiDoc MP with fluorescein settings.

RNase A completely degraded the RNA but was inhibited to varying degrees by the various inhibitors; Murine inhibitor lost all protective ability with heating at 70° C. and SUPERase-In at ~80° C., whereas the aptamer inhibitor maintained complete protection despite even 95° C. treatment (see FIG. 8A-8B).

Example 7: RNase Activity in Biological Samples Prevents RT-LAMP. RT-LAMP Activity was Rescued by Aptamers that Inhibit RNases RT-LAMP reactions were performed following manufacturer instructions (New England Biolabs, Ipswich, MA). These were performed at 65° C. using WarmStart® LAMP Mix (New England Biolabs, Ipswich, MA), Jurkat RNA and primers for human ACTB. The amounts of the biological samples (urine and serum) were increased and RT LAMP activity measured.

100% activity of RNase was set by the control under 0% sample conditions and provided no detectable amplification in the time course of the experiment (90 minutes). Aptamer inhibitors of RNase A was able to offer complete protection to 1.25% v/v of urine or serum whereas SUPERase-IN and Murine RNA inhibitors resulted in only 50% or less of the amplification product compared to aptamers. In these assays, Murine inhibitor offered more protection to RNA than SUPERase-IN but significantly less than the aptamer in urine and provided similar protection to the aptamers at 1.25% serum (see FIG. 8A-8B).

Example 9: Aptamers that Inhibit RNase Activity Protect mRNA Produced by In Vitro Transcription as Determined by RT-QPCR IVT reactions were performed at 50° C. for 1 hour using 140 ng Hi-T7® RNA Polymerase (New England Biolabs, Ipswich, MA), 0.5 mg CLuc DNA, and 0.5 mM NTPs. Each reaction was incubated with +/− RNase A inhibitor (1 mM aptamer or Murine) and a 2-fold serial dilution of RNase A from 1 ng-2 pg.

Aptamer and Murine inhibitors protected the RNA product from digestion up to 0.5 ng RNase A.

Figure 10C:
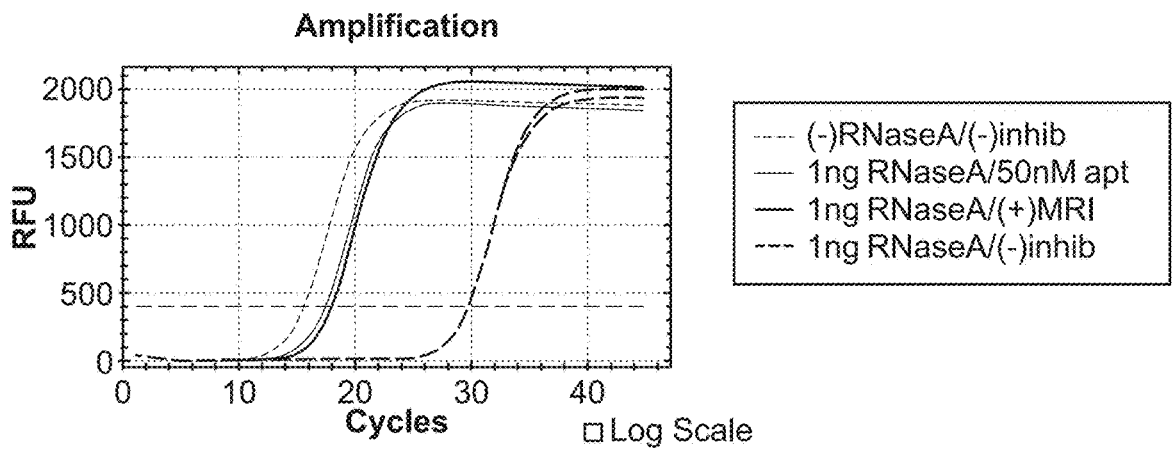

RT-qPCR reactions were performed using Luna® Universal One Step RT-qPCR mix (New England Biolabs, Ipswich, MA), primers to ACTB and Jurkat total RNA with fluorescence detection and indicated amounts of RNase A or RNase I added with or without RNase inhibitor aptamer. Aptamers were able to protect the RNA and enable RT-qPCR in with up to 1 ng RNase A and 200 ng RNase I without affecting performance of the qPCR reaction (see for example, FIG. 10A-10C).

What is claimed is:

1. A composition comprising: a single stranded oligonucleotide RNase inhibitor that inhibits the activity of at least one of RNase A and RNase I wherein the RNase inhibitor is selected from the group consisting of:
   (a) an oligonucleotide having at least 90% sequence identity with a sequence selected from any of SEQ ID NOs: 1-62; and
   (b) an oligonucleotide having at least 90% sequence identity with a sequence selected from any of SEQ ID NOs: 1-62, further comprising one or more hydrophobic nucleotide substitutions in the oligonucleotide.

2. A composition according to claim 1, wherein the oligonucleotide has a sequence corresponding to any of the oligonucleotides in SEQ ID. Nos 1-62 further comprising one or more hydrophobic nucleotide substitutions in the oligonucleotide.

3. A composition according to claim 1, wherein the one or more hydrophobic nucleotide substitutions are selected from the group consisting of 5-(N-benzylcarboxyamide)-dUTP (BndUTP), 5-(N-isobutylcarboxyamide)-dUTP (iBudUTP), or 5-(N-tryptaminocarboxyamide)-dUTP (Trp dUTP) and Napthyl-dU.

4. The composition according to claim 1, wherein the RNase inhibitor is in a solution, immobilized on a matrix or in powder form resulting from freeze drying or lyophilization of the inhibitor preparation.

5. The composition according to claim 4, wherein the matrix is selected from the group consisting of a bead, a reaction vessel, or a multiwell plate.

6. A kit containing a reaction vessel for receiving a sample suspected of containing an RNase, the reaction vessel containing the composition according to claim 1, that is either immobilized or in solution or dried wherein the dried formulation is suitable for receiving a sample containing a target RNA.

7. A method for protecting an RNA in a sample from degradation by an RNase, comprising: combining a composition according to claim 1 with a sample containing RNA or a reaction mixture for adding to or synthesizing RNA.

8. The method according to claim 7, further comprising reverse transcribing the RNA with a reverse transcriptase to form DNA and amplifying the DNA for subsequent detection, diagnosis of the RNA, purification or sequencing.

9. The method according to claim 7, further comprising synthesizing an RNA by means of an RNA polymerase or including an RNA polymerase in the reaction mixture for synthesizing RNA.

10. The method according to claim 7, wherein the RNA is obtained from a biological sample.

11. The method according to claim 7, wherein the RNA is one or more RNAs selected from the group consisting of messenger RNA, transfer RNA, ribosomal RNA, microRNA, long non coding RNA, antisense RNA, CRISPR RNA, Piwi interacting RNA, small interfering RNAs, 7SK RNA, enhancer RNA, spliced leader RNA, telomerase RNA component, guide RNA, small nuclear RNA, small nucleolar RNA, ectosomal RNA, and viral RNA.

* * * * *

SEQUENCE LISTING

<160> NUMBER OF SEQ ID NOS: 62

<210> SEQ ID NO 1
<211> LENGTH: 61
<212> TYPE: DNA
<213> ORGANISM: Artificial Sequence
<220> FEATURE:
<223> OTHER INFORMATION: Synthetic construct

<400> SEQUENCE: 1
cagtctgagg aacatataaa cggctctgga ctatattgtg agaatggcgt ccctcagact    60
g                                                                   61

<210> SEQ ID NO 2
<211> LENGTH: 60
<212> TYPE: DNA
<213> ORGANISM: Artificial Sequence
<220> FEATURE:
<223> OTHER INFORMATION: Synthetic construct

<400> SEQUENCE: 2
cagtctgagg attagaggac tagaattggg gcgtttaggg cggtggggac cctcagactg    60

<210> SEQ ID NO 3
<211> LENGTH: 62
<212> TYPE: DNA
<213> ORGANISM: Artificial Sequence
<220> FEATURE:
<223> OTHER INFORMATION: Synthetic construct

<400> SEQUENCE: 3
cagtctgagg ccatggtcac cattgagtac cttgccctcg tttaaccgcg ggcctcagac    60
tg                                                                  62

<210> SEQ ID NO 4
<211> LENGTH: 60
<212> TYPE: DNA
<213> ORGANISM: Artificial Sequence
<220> FEATURE:
<223> OTHER INFORMATION: Synthetic construct

<400> SEQUENCE: 4
cagtctgagg gggttgttga atggtttata aacaaggcga tacaatcatc cctcagactg    60

<210> SEQ ID NO 5
<211> LENGTH: 61
<212> TYPE: DNA
<213> ORGANISM: Artificial Sequence
<220> FEATURE:
<223> OTHER INFORMATION: Synthetic construct

<400> SEQUENCE: 5
cagtctgagg tatacctcct tatatagacc tcgattgccg acgcaggcta acctcagact    60
g                                                                   61

<210> SEQ ID NO 6
<211> LENGTH: 62
<212> TYPE: DNA
<213> ORGANISM: Artificial Sequence
<220> FEATURE:
<223> OTHER INFORMATION: Synthetic construct

<400> SEQUENCE: 6
cagtctgagg tcaagatgca cttgagacct cgaatacttc catagatagg ctcctcagac    60
tg                                                              62

<210> SEQ ID NO 7
<211> LENGTH: 61
<212> TYPE: DNA
<213> ORGANISM: Artificial Sequence
<220> FEATURE:
<223> OTHER INFORMATION: Synthetic construct

<400> SEQUENCE: 7
cagtctgagg cctcagccgc tgggtaaggt ttagcggttg gcagggatga gcctcagact    60
g                                                                    61

<210> SEQ ID NO 8
<211> LENGTH: 63
<212> TYPE: DNA
<213> ORGANISM: Artificial Sequence
<220> FEATURE:
<223> OTHER INFORMATION: Synthetic construct

<400> SEQUENCE: 8
cagtctgagg attgcggaca cgcacaattt ggggcctttg ggacaggtgg gggcctcaga    60
ctg                                                                  63

<210> SEQ ID NO 9
<211> LENGTH: 61
<212> TYPE: DNA
<213> ORGANISM: Artificial Sequence
<220> FEATURE:
<223> OTHER INFORMATION: Synthetic construct

<400> SEQUENCE: 9
cagtctgagg aagctactga tatcgtggat gtggatggca ggtctacagt gcctcagact    60
g                                                                    61

<210> SEQ ID NO 10
<211> LENGTH: 62
<212> TYPE: DNA
<213> ORGANISM: Artificial Sequence
<220> FEATURE:
<223> OTHER INFORMATION: Synthetic construct

<400> SEQUENCE: 10
cagtctgagg acacaagagg ttcgaatgca tttcgaacat ctgtatcaac accctcagac    60
tg                                                                   62

<210> SEQ ID NO 11
<211> LENGTH: 86
<212> TYPE: DNA
<213> ORGANISM: Artificial Sequence
<220> FEATURE:
<223> OTHER INFORMATION: Synthetic construct

<400> SEQUENCE: 11
agcagtccga agtgagtgac acattagacc tatgtcgtga gtgtttatgg ggtcgcatcc    60
tacacagtcg ctgcgtagca agtaca                                         86

<210> SEQ ID NO 12
<211> LENGTH: 86
<212> TYPE: DNA
<213> ORGANISM: Artificial Sequence
<220> FEATURE:

<223> OTHER INFORMATION: Synthetic construct

<400> SEQUENCE: 12
agcagtccga agtgagtgac tcgcttgggt acatttaact ggtagaggtt taggaagcta    60
ctaagagtcg ctgcgtagca agtaca    86

<210> SEQ ID NO 13
<211> LENGTH: 85
<212> TYPE: DNA
<213> ORGANISM: Artificial Sequence
<220> FEATURE:
<223> OTHER INFORMATION: Synthetic construct

<400> SEQUENCE: 13
agcagtccga agtgagtgac cggccgtggt ctggactata ttgtgagaat ccagccgtgg    60
agggagtcgc tgcgtagcaa gtaca    85

<210> SEQ ID NO 14
<211> LENGTH: 86
<212> TYPE: DNA
<213> ORGANISM: Artificial Sequence
<220> FEATURE:
<223> OTHER INFORMATION: Synthetic construct

<400> SEQUENCE: 14
agcagtccga agtgagtgac tgtttatcag acactcactc atggtgggtt tttcacctat    60
atcggagtcg ctgcgtagca agtaca    86

<210> SEQ ID NO 15
<211> LENGTH: 86
<212> TYPE: DNA
<213> ORGANISM: Artificial Sequence
<220> FEATURE:
<223> OTHER INFORMATION: Synthetic construct

<400> SEQUENCE: 15
agcagtccga agtgagtgac tctgtccatc actcagcgat ttatgggtct atgcaattat    60
gagtgagtcg ctgcgtagca agtaca    86

<210> SEQ ID NO 16
<211> LENGTH: 86
<212> TYPE: DNA
<213> ORGANISM: Artificial Sequence
<220> FEATURE:
<223> OTHER INFORMATION: Synthetic construct

<400> SEQUENCE: 16
agcagtccga agtgagtgac taagtagggt tttttaaacc cggccgcgcc tttaaagcgg    60
tacttagtcg ctgcgtagca agtaca    86

<210> SEQ ID NO 17
<211> LENGTH: 85
<212> TYPE: DNA
<213> ORGANISM: Artificial Sequence
<220> FEATURE:
<223> OTHER INFORMATION: Synthetic construct

<400> SEQUENCE: 17
agcagtccga agtgagtgac atcgagccct cgagtgccct caaatgacac tcatgaaatc    60
cctcagtcgc tgcgtagcaa gtaca    85

```
<210> SEQ ID NO 18
<211> LENGTH: 86
<212> TYPE: DNA
<213> ORGANISM: Artificial Sequence
<220> FEATURE:
<223> OTHER INFORMATION: Synthetic construct

<400> SEQUENCE: 18
agcagtccga agtgagtgac tgtgcagtaa gttttaacc cctgcatacc ggctttatgc      60
cggtcagtcg ctgcgtagca agtaca                                          86

<210> SEQ ID NO 19
<211> LENGTH: 86
<212> TYPE: DNA
<213> ORGANISM: Artificial Sequence
<220> FEATURE:
<223> OTHER INFORMATION: Synthetic construct

<400> SEQUENCE: 19
agcagtccga agtgagtgac aactggtggg tgggtgggat gtgtgattct aaatgttgca      60
ctccgagtcg ctgcgtagca agtaca                                          86

<210> SEQ ID NO 20
<211> LENGTH: 85
<212> TYPE: DNA
<213> ORGANISM: Artificial Sequence
<220> FEATURE:
<223> OTHER INFORMATION: Synthetic construct

<400> SEQUENCE: 20
agcagtccga agtgagtgac ttaatctcat taagaattag cctgtactta tgcgcacacc      60
ctagagtcgc tgcgtagcaa gtaca                                           85

<210> SEQ ID NO 21
<211> LENGTH: 86
<212> TYPE: DNA
<213> ORGANISM: Artificial Sequence
<220> FEATURE:
<223> OTHER INFORMATION: Synthetic construct

<400> SEQUENCE: 21
agcagtccga agtgagtgac tcattcgaat gcatttcgaa catctatatc agcggaaaca      60
aggaaagtcg ctgcgtagca agtaca                                          86

<210> SEQ ID NO 22
<211> LENGTH: 88
<212> TYPE: DNA
<213> ORGANISM: Artificial Sequence
<220> FEATURE:
<223> OTHER INFORMATION: Synthetic construct

<400> SEQUENCE: 22
agcagtccga agtgagtgac atgaacctca tatcattaag tattagcgct cattataggg      60
ttccaaaagt cgctgcgtag caagtaca                                        88

<210> SEQ ID NO 23
<211> LENGTH: 86
<212> TYPE: DNA
<213> ORGANISM: Artificial Sequence
<220> FEATURE:
<223> OTHER INFORMATION: Synthetic construct

<400> SEQUENCE: 23
```
agcagtccga agtgagtgac aggtgaatct cattacagaa ttagccgtaa ttatcacctc    60
aaggcagtcg ctgcgtagca agtaca                                        86

<210> SEQ ID NO 24
<211> LENGTH: 86
<212> TYPE: DNA
<213> ORGANISM: Artificial Sequence
<220> FEATURE:
<223> OTHER INFORMATION: Synthetic construct

<400> SEQUENCE: 24
agcagtccga agtgagtgac tataggtgca attaaaatcg gaacatgta actccgggaa    60 gcgtaagtcg ctgcgtagca agtaca                                        86

<210> SEQ ID NO 25
<211> LENGTH: 86
<212> TYPE: DNA
<213> ORGANISM: Artificial Sequence
<220> FEATURE:
<223> OTHER INFORMATION: Synthetic construct

<400> SEQUENCE: 25
agcagtccga agtgagtgac cctgcgccct agatggattt agggacttgt gagggcctac    60
tgggaagtcg ctgcgtagca agtaca                                        86

<210> SEQ ID NO 26
<211> LENGTH: 86
<212> TYPE: DNA
<213> ORGANISM: Artificial Sequence
<220> FEATURE:
<223> OTHER INFORMATION: Synthetic construct

<400> SEQUENCE: 26
agcagtccga agtgagtgac accttgtctg ctctaggtgg tcatggttta ggcctttgaa    60
aaataagtcg ctgcgtagca agtaca                                        86

<210> SEQ ID NO 27
<211> LENGTH: 88
<212> TYPE: DNA
<213> ORGANISM: Artificial Sequence
<220> FEATURE:
<223> OTHER INFORMATION: Synthetic construct

<400> SEQUENCE: 27
agcagtccga agtgagtgac tcaatatcgg taggtttcgc tcatagtatg gaaaatccac    60
agagtacagt cgctgcgtag caagtaca                                      88

<210> SEQ ID NO 28
<211> LENGTH: 42
<212> TYPE: DNA
<213> ORGANISM: Artificial Sequence
<220> FEATURE:
<223> OTHER INFORMATION: Synthetic construct

<400> SEQUENCE: 28
ttcgaatgca tttcgaacat ctgtatcaac accctcagac tg                      42

<210> SEQ ID NO 29
<211> LENGTH: 30
<212> TYPE: DNA
<213> ORGANISM: Artificial Sequence
<220> FEATURE:
<223> OTHER INFORMATION: Synthetic construct

<400> SEQUENCE: 29
ttcgaatgca tttcgaacat ctgtatcaac                              30

<210> SEQ ID NO 30
<211> LENGTH: 34
<212> TYPE: DNA
<213> ORGANISM: Artificial Sequence
<220> FEATURE:
<223> OTHER INFORMATION: Synthetic construct

<400> SEQUENCE: 30
ttcgaatgca tttcgaacat ctgtatcaac accc                         34

<210> SEQ ID NO 31
<211> LENGTH: 30
<212> TYPE: DNA
<213> ORGANISM: Artificial Sequence
<220> FEATURE:
<223> OTHER INFORMATION: Synthetic construct

<400> SEQUENCE: 31
ttcgaatgca tttcgaacat ctatatcagc                              30

<210> SEQ ID NO 32
<211> LENGTH: 88
<212> TYPE: DNA
<213> ORGANISM: Artificial Sequence
<220> FEATURE:
<223> OTHER INFORMATION: Synthetic construct

<400> SEQUENCE: 32
agcaagagcc tgcctgtccc ctgtcttaga ccgcaaatgc acgtctgcct gtttgggacg    60
tcctacgccc atcatctact aaaaaaaa                                      88

<210> SEQ ID NO 33
<211> LENGTH: 90
<212> TYPE: DNA
<213> ORGANISM: Artificial Sequence
<220> FEATURE:
<223> OTHER INFORMATION: Synthetic construct

<400> SEQUENCE: 33
agcaagagcc tgcctgtctg ctactctgct ctaagtcatt aatgctccgt aaacagcaga    60
cgacctacgc ccatcatcta ctaaaaaaaa                                    90

<210> SEQ ID NO 34
<211> LENGTH: 90
<212> TYPE: DNA
<213> ORGANISM: Artificial Sequence
<220> FEATURE:
<223> OTHER INFORMATION: Synthetic construct

<400> SEQUENCE: 34
agcaagagcc tgcctgtctg tcgcctccgt tccagtatac attacctggt taaaccttgg    60
caacctacgc ccatcatcta ctaaaaaaaa                                    90

<210> SEQ ID NO 35
<211> LENGTH: 90
<212> TYPE: DNA
<213> ORGANISM: Artificial Sequence
<220> FEATURE:
<223> OTHER INFORMATION: Synthetic construct

<400> SEQUENCE: 35
agcaagagcc tgcctgtcgc ctcagcgtgt cactgcgtcg agggactgca gagccggtag    60
ccacctacgc ccatcatcta ctaaaaaaaa                                     90

<210> SEQ ID NO 36
<211> LENGTH: 90
<212> TYPE: DNA
<213> ORGANISM: Artificial Sequence
<220> FEATURE:
<223> OTHER INFORMATION: Synthetic construct

<400> SEQUENCE: 36
agcaagagcc tgcctgtctt gtaacaccct gccatccgtt ccgacacggt ctaccactta    60
aagcctacgc ccatcatcta ctaaaaaaaa                                     90

<210> SEQ ID NO 37
<211> LENGTH: 90
<212> TYPE: DNA
<213> ORGANISM: Artificial Sequence
<220> FEATURE:
<223> OTHER INFORMATION: Synthetic construct

<400> SEQUENCE: 37
agcaagagcc tgcctgtctc cgttccgatc caatctggat ttaacacttg acgggccaac    60
cgacctacgc ccatcatcta ctaaaaaaaa                                     90

<210> SEQ ID NO 38
<211> LENGTH: 90
<212> TYPE: DNA
<213> ORGANISM: Artificial Sequence
<220> FEATURE:
<223> OTHER INFORMATION: Synthetic construct

<400> SEQUENCE: 38
agcaagagcc tgcctgtcgc ctcagcgtgt cactgcgtcg agggactgca gagccggtag    60
tctcctacgc ccatcatcta ctaaaaaaaa                                     90

<210> SEQ ID NO 39
<211> LENGTH: 90
<212> TYPE: DNA
<213> ORGANISM: Artificial Sequence
<220> FEATURE:
<223> OTHER INFORMATION: Synthetic construct

<400> SEQUENCE: 39
agcaagagcc tgcctgtctt gtaatgcctc cgtgaactaa tcccccagcg cgcctacttg    60
gctcctacgc ccatcatcta ctaaaaaaaa                                     90

<210> SEQ ID NO 40
<211> LENGTH: 90
<212> TYPE: DNA
<213> ORGANISM: Artificial Sequence
<220> FEATURE:
<223> OTHER INFORMATION: Synthetic construct

<400> SEQUENCE: 40
agcaagagcc tgcctgtctg cacatctcca atacttgcca ctgctccgtt aacgcctgca    60
gtacctacgc ccatcatcta ctaaaaaaaa                                     90

<210> SEQ ID NO 41
<211> LENGTH: 89

```
<212> TYPE: DNA
<213> ORGANISM: Artificial Sequence
<220> FEATURE:
<223> OTHER INFORMATION: Synthetic construct

<400> SEQUENCE: 41
agcaagagcc tgcctgtctc taccccgcgc cattccagcg tatgctggct ggtttaacgg    60
gacctacgcc catcatctac taaaaaaaa                                      89

<210> SEQ ID NO 42
<211> LENGTH: 90
<212> TYPE: DNA
<213> ORGANISM: Artificial Sequence
<220> FEATURE:
<223> OTHER INFORMATION: Synthetic construct

<400> SEQUENCE: 42
agcaagagcc tgcctgtctc taatcctgac gcttgtgcag gatgtagcaa acagttaaac    60
gaacctacgc ccatcatcta ctaaaaaaaa                                     90

<210> SEQ ID NO 43
<211> LENGTH: 90
<212> TYPE: DNA
<213> ORGANISM: Artificial Sequence
<220> FEATURE:
<223> OTHER INFORMATION: Synthetic construct

<400> SEQUENCE: 43
agcaagagcc tgcctgtcgc ctcagcgtgt cactgcgtcg agggactgca gagccggtag    60
tcacctacgc ccatcatcta ctaaaaaaaa                                     90

<210> SEQ ID NO 44
<211> LENGTH: 88
<212> TYPE: DNA
<213> ORGANISM: Artificial Sequence
<220> FEATURE:
<223> OTHER INFORMATION: Synthetic construct

<400> SEQUENCE: 44
agcaagagcc tgcctgtcct ttaagaacac ggcgtgcgtc ttcagcgcgc ctagctgcca    60
gcctacgccc atcatctact aaaaaaaa                                       88

<210> SEQ ID NO 45
<211> LENGTH: 90
<212> TYPE: DNA
<213> ORGANISM: Artificial Sequence
<220> FEATURE:
<223> OTHER INFORMATION: Synthetic construct

<400> SEQUENCE: 45
agcaagagcc tgcctgtcgt cgaccctagc tttgaacact gccggtgtgg atcacggaca    60
aggcctacgc ccatcatcta ctaaaaaaaa                                     90

<210> SEQ ID NO 46
<211> LENGTH: 43
<212> TYPE: DNA
<213> ORGANISM: Artificial Sequence
<220> FEATURE:
<223> OTHER INFORMATION: Synthetic construct

<400> SEQUENCE: 46
cctgtcccct gtcttagacc gcaaatgcac gtctgcctgt ttg                      43
```

```
<210> SEQ ID NO 47
<211> LENGTH: 43
<212> TYPE: DNA
<213> ORGANISM: Artificial Sequence
<220> FEATURE:
<223> OTHER INFORMATION: Synthetic construct

<400> SEQUENCE: 47
tcccctgtct tagaccgcaa atgcacgtct gcctgtttgg gac            43

<210> SEQ ID NO 48
<211> LENGTH: 45
<212> TYPE: DNA
<213> ORGANISM: Artificial Sequence
<220> FEATURE:
<223> OTHER INFORMATION: Synthetic construct

<400> SEQUENCE: 48
tctgtcgcct ccgttccagt atacattacc tggttaaacc ttggc          45

<210> SEQ ID NO 49
<211> LENGTH: 45
<212> TYPE: DNA
<213> ORGANISM: Artificial Sequence
<220> FEATURE:
<223> OTHER INFORMATION: Synthetic construct

<400> SEQUENCE: 49
tcgcctccgt tccagtatac attacctggt taaaccttgg caacc          45

<210> SEQ ID NO 50
<211> LENGTH: 45
<212> TYPE: DNA
<213> ORGANISM: Artificial Sequence
<220> FEATURE:
<223> OTHER INFORMATION: Synthetic construct

<400> SEQUENCE: 50
agcaagagcc tgcctgtcgc ctcagcgtgt cactgcgtcg aggga          45

<210> SEQ ID NO 51
<211> LENGTH: 45
<212> TYPE: DNA
<213> ORGANISM: Artificial Sequence
<220> FEATURE:
<223> OTHER INFORMATION: Synthetic construct

<400> SEQUENCE: 51
agagcctgcc tgtcgcctca gcgtgtcact gcgtcgaggg actgc          45

<210> SEQ ID NO 52
<211> LENGTH: 45
<212> TYPE: DNA
<213> ORGANISM: Artificial Sequence
<220> FEATURE:
<223> OTHER INFORMATION: Synthetic construct

<400> SEQUENCE: 52
cctgcctgtc gcctcagcgt gtcactgcgt cgagggactg cagag          45

<210> SEQ ID NO 53
<211> LENGTH: 45
<212> TYPE: DNA
<213> ORGANISM: Artificial Sequence
<220> FEATURE:
<223> OTHER INFORMATION: Synthetic construct
```

<400> SEQUENCE: 53
cctgtcgcct cagcgtgtca ctgcgtcgag ggactgcaga gccgg          45

<210> SEQ ID NO 54
<211> LENGTH: 45
<212> TYPE: DNA
<213> ORGANISM: Artificial Sequence
<220> FEATURE:
<223> OTHER INFORMATION: Synthetic construct

<400> SEQUENCE: 54
tcgcctcagc gtgtcactgc gtcgagggac tgcagagccg gtagc          45

<210> SEQ ID NO 55
<211> LENGTH: 45
<212> TYPE: DNA
<213> ORGANISM: Artificial Sequence
<220> FEATURE:
<223> OTHER INFORMATION: Synthetic construct

<400> SEQUENCE: 55
agcaagagcc tgcctgtcgc ctcagcgtgt cactgcgtcg aggga          45

<210> SEQ ID NO 56
<211> LENGTH: 45
<212> TYPE: DNA
<213> ORGANISM: Artificial Sequence
<220> FEATURE:
<223> OTHER INFORMATION: Synthetic construct

<400> SEQUENCE: 56
agagcctgcc tgtcgcctca gcgtgtcact gcgtcgaggg actgc          45

<210> SEQ ID NO 57
<211> LENGTH: 45
<212> TYPE: DNA
<213> ORGANISM: Artificial Sequence
<220> FEATURE:
<223> OTHER INFORMATION: Synthetic construct

<400> SEQUENCE: 57
cctgcctgtc gcctcagcgt gtcactgcgt cgagggactg cagag          45

<210> SEQ ID NO 58
<211> LENGTH: 45
<212> TYPE: DNA
<213> ORGANISM: Artificial Sequence
<220> FEATURE:
<223> OTHER INFORMATION: Synthetic construct

<400> SEQUENCE: 58
cctgtcgcct cagcgtgtca ctgcgtcgag ggactgcaga gccgg          45

<210> SEQ ID NO 59
<211> LENGTH: 43
<212> TYPE: DNA
<213> ORGANISM: Artificial Sequence
<220> FEATURE:
<223> OTHER INFORMATION: Synthetic construct

<400> SEQUENCE: 59
ttaagaacac ggcgtgcgtc ttcagcgcgc ctagctgcca gcc            43

<210> SEQ ID NO 60

```
<211> LENGTH: 43
<212> TYPE: DNA
<213> ORGANISM: Artificial Sequence
<220> FEATURE:
<223> OTHER INFORMATION: Synthetic construct

<400> SEQUENCE: 60
gaacacggcg tgcgtcttca gcgcgcctag ctgccagcct acg            43

<210> SEQ ID NO 61
<211> LENGTH: 43
<212> TYPE: DNA
<213> ORGANISM: Artificial Sequence
<220> FEATURE:
<223> OTHER INFORMATION: Synthetic construct

<400> SEQUENCE: 61
acggcgtgcg tcttcagcgc gcctagctgc cagcctacgc cca            43

<210> SEQ ID NO 62
<211> LENGTH: 30
<212> TYPE: DNA
<213> ORGANISM: Artificial Sequence
<220> FEATURE:
<223> OTHER INFORMATION: Synthetic construct

<400> SEQUENCE: 62
ttcgaatgca tttcgaacat ctrtatcarc                            30
```